(12) United States Patent
Giordano et al.

(10) Patent No.: US 9,788,931 B2
(45) Date of Patent: Oct. 17, 2017

(54) HOLDER FOR HEART VALVE PROSTHESES, CORRESPONDING STORAGE ARRANGEMENT, DELIVERY INSTRUMENT AND KIT

(71) Applicant: Sorin Group Italia S.r.l., Milan (IT)

(72) Inventors: Giovanni Giordano, Cuneo (IT); Paolo Gaschino, Castagneto Po (IT); Giovanni Rolando, Chivasso (IT); Arnaldo Giannetti, Crescentino (IT)

(73) Assignee: Sorin Group Italia S.r.l., Milan (IT)

( * ) Notice: Subject to any disclaimer, the term of this patent is extended or adjusted under 35 U.S.C. 154(b) by 0 days.

(21) Appl. No.: 14/998,237

(22) Filed: Dec. 23, 2015

(65) Prior Publication Data

US 2016/0128819 A1    May 12, 2016

Related U.S. Application Data

(63) Continuation of application No. PCT/IB2014/064804, filed on Sep. 24, 2014.

(51) Int. Cl.

| | |
|---|---|
| *A61F 2/00* | (2006.01) |
| *A61B 50/30* | (2016.01) |
| *B65D 81/02* | (2006.01) |
| *B65D 81/18* | (2006.01) |
| *A61F 2/24* | (2006.01) |
| *A61F 2/95* | (2013.01) |

(52) U.S. Cl.
CPC ............ *A61F 2/0095* (2013.01); *A61B 50/30* (2016.02); *A61F 2/2418* (2013.01);
(Continued)

(58) Field of Classification Search
CPC ... A61B 50/30; A61B 2050/3005; A61F 2/00; A61F 2/0095; A61F 2/24; A61F 2/2412;
(Continued)

(56) References Cited

U.S. PATENT DOCUMENTS 5,800,531 A * 9/1998 Cosgrove .............. A61F 2/2412
                                                    623/2.11
5,824,068 A * 10/1998 Bugge ................... A61F 2/0095
                                                    623/2.11

(Continued)

FOREIGN PATENT DOCUMENTS

EP    1935377 A1    6/2008
EP    1690515 B1    7/2008

(Continued)

OTHER PUBLICATIONS

International Search Report issued in PCT/IB2014/064804, mailed Jun. 1, 2015, 3 pages.

(Continued)

*Primary Examiner* — Bryon Gehman
(74) *Attorney, Agent, or Firm* — Faegre Baker Daniels LLP

(57) ABSTRACT

A holder for heart valve prostheses, the holder including a hub portion having a longitudinal axis, an engagement portion coupled to the hub portion and including plural L-shaped finger members variably positionable relative to the hub portion between a collapsed condition wherein the finger members are closed onto the hub portion and an expanded condition wherein the finger members radially protrude with respect to the hub portion to engage a heart valve prosthesis.

20 Claims, 15 Drawing Sheets

(52) U.S. Cl.
CPC .......... *A61F 2/2427* (2013.01); *A61F 2/2436* (2013.01); *B65D 81/02* (2013.01); *B65D 81/18* (2013.01); *A61B 2050/3005* (2016.02); *A61F 2/2412* (2013.01); *A61F 2002/9522* (2013.01)

(58) Field of Classification Search
CPC .... A61F 2/2418; A61F 2/2427; A61F 2/2436; A61F 2002/9522; B65D 81/02; B65D 81/18
USPC ........ 206/210, 363, 438, 570; 623/2.1, 2.11, 623/2.13
See application file for complete search history.

(56) References Cited

U.S. PATENT DOCUMENTS

| | | | |
|---|---|---|---|
| 6,214,043 B1 * | 4/2001 | Krueger | A61F 2/2427 623/2.11 |
| 7,389,874 B2 * | 6/2008 | Quest | A61F 2/2427 206/210 |
| 8,747,458 B2 * | 6/2014 | Tuval | A61F 2/0095 623/1.11 |
| 9,114,010 B2 * | 8/2015 | Gaschino | A61F 2/0095 |
| 9,585,752 B2 * | 3/2017 | Chang | A61F 2/2427 |
| 2009/0054976 A1 | 2/2009 | Tuval et al. | |

FOREIGN PATENT DOCUMENTS

| | | |
|---|---|---|
| EP | 2119417 A2 | 11/2009 |
| EP | 2644158 A1 | 10/2013 |
| WO | 2012106491 A1 | 8/2012 |
| WO | 2016046599 A1 | 3/2016 |

OTHER PUBLICATIONS

Written Opinion of the International Searching Authority issued in PCT/IB2014/064804, mailed Jun. 1, 2015, 5 pages.

\* cited by examiner

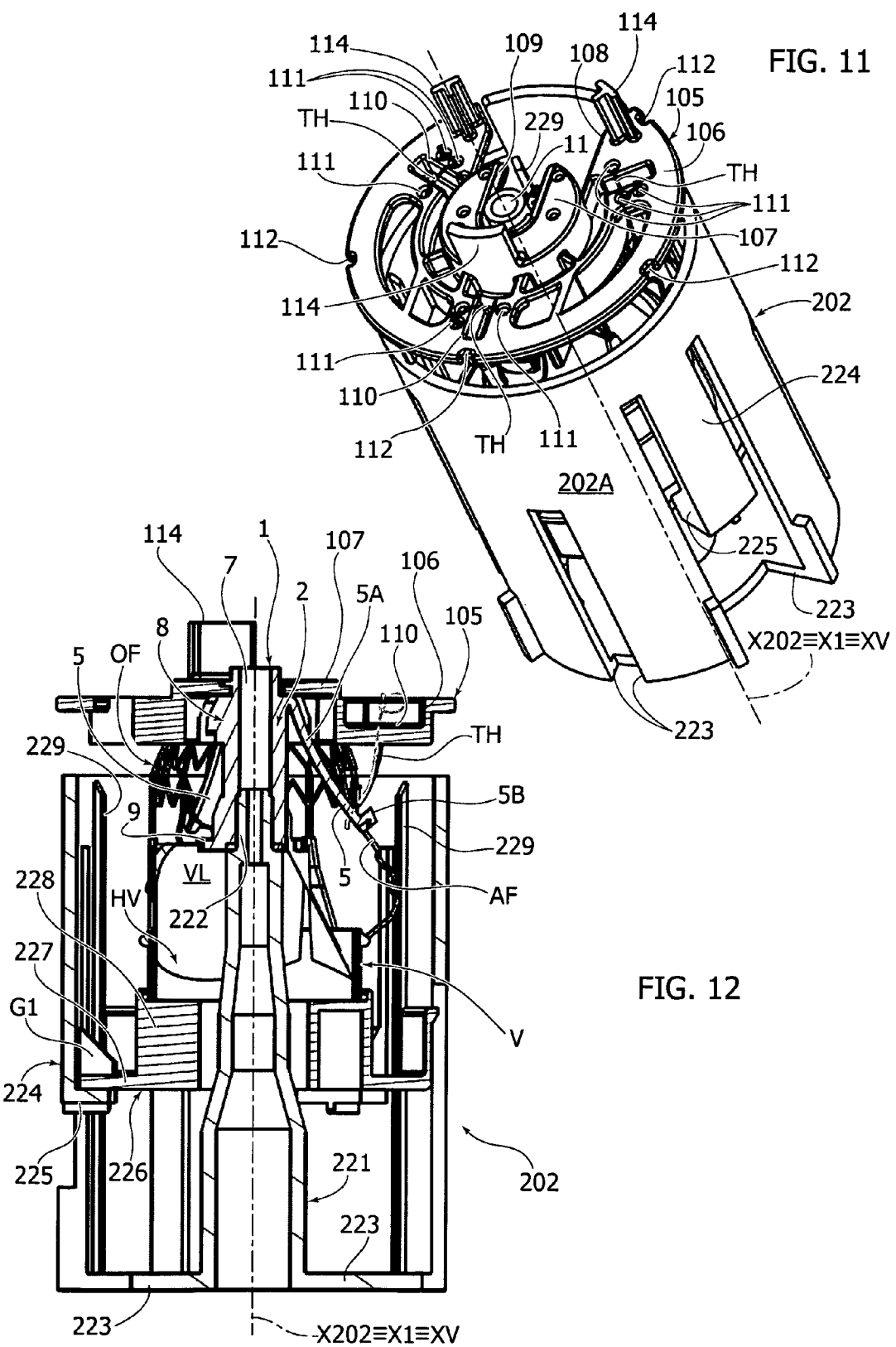

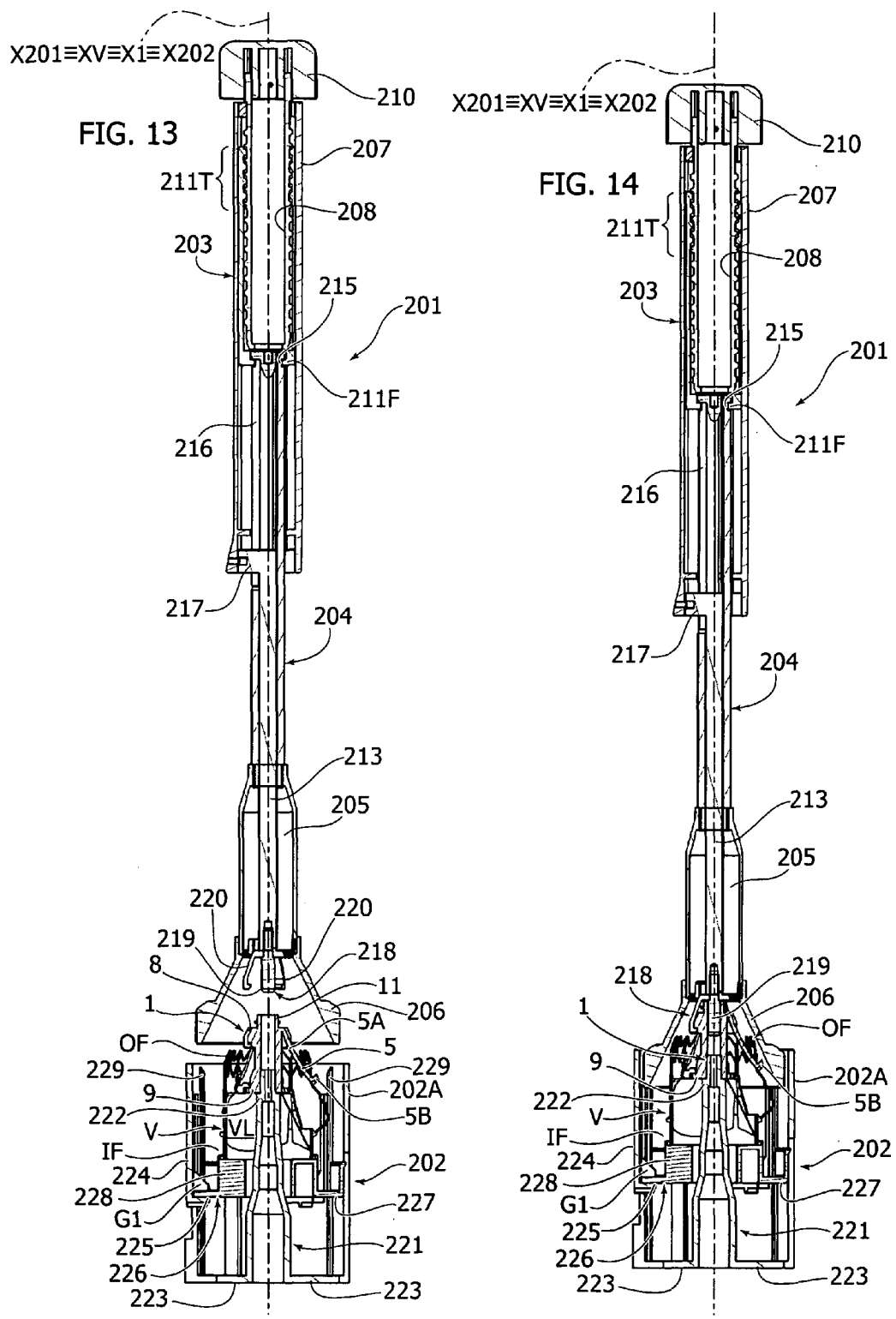

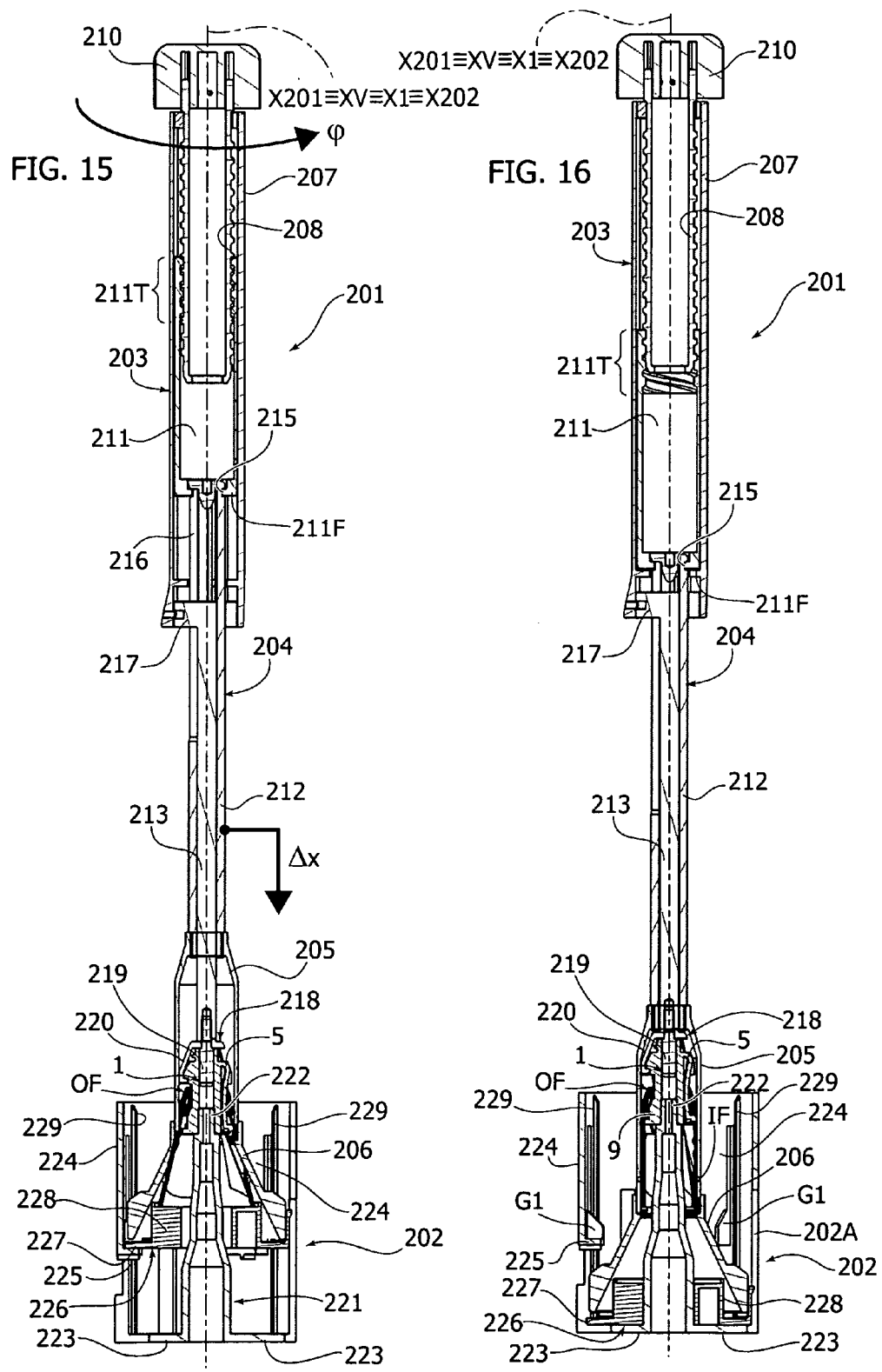

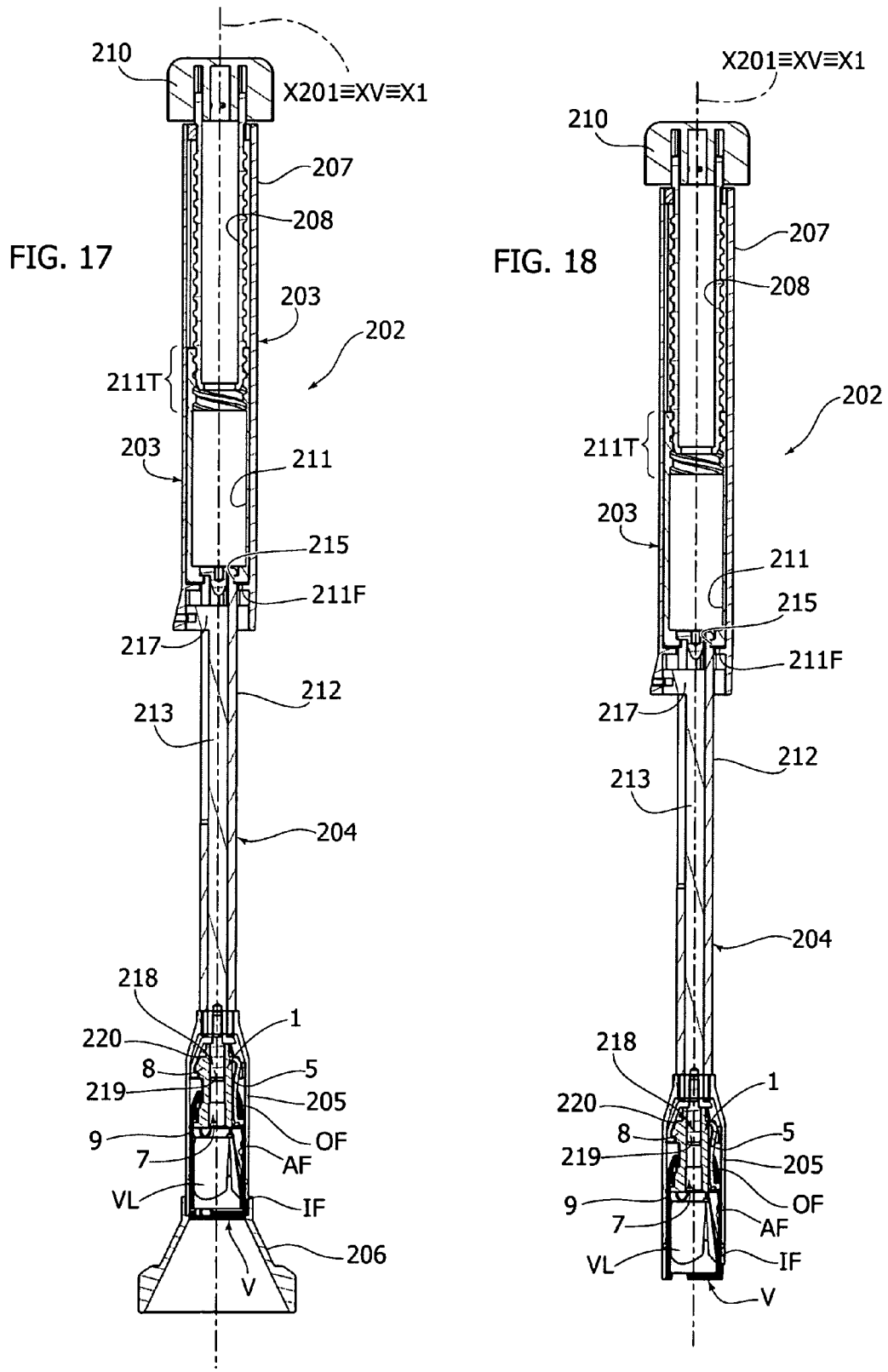

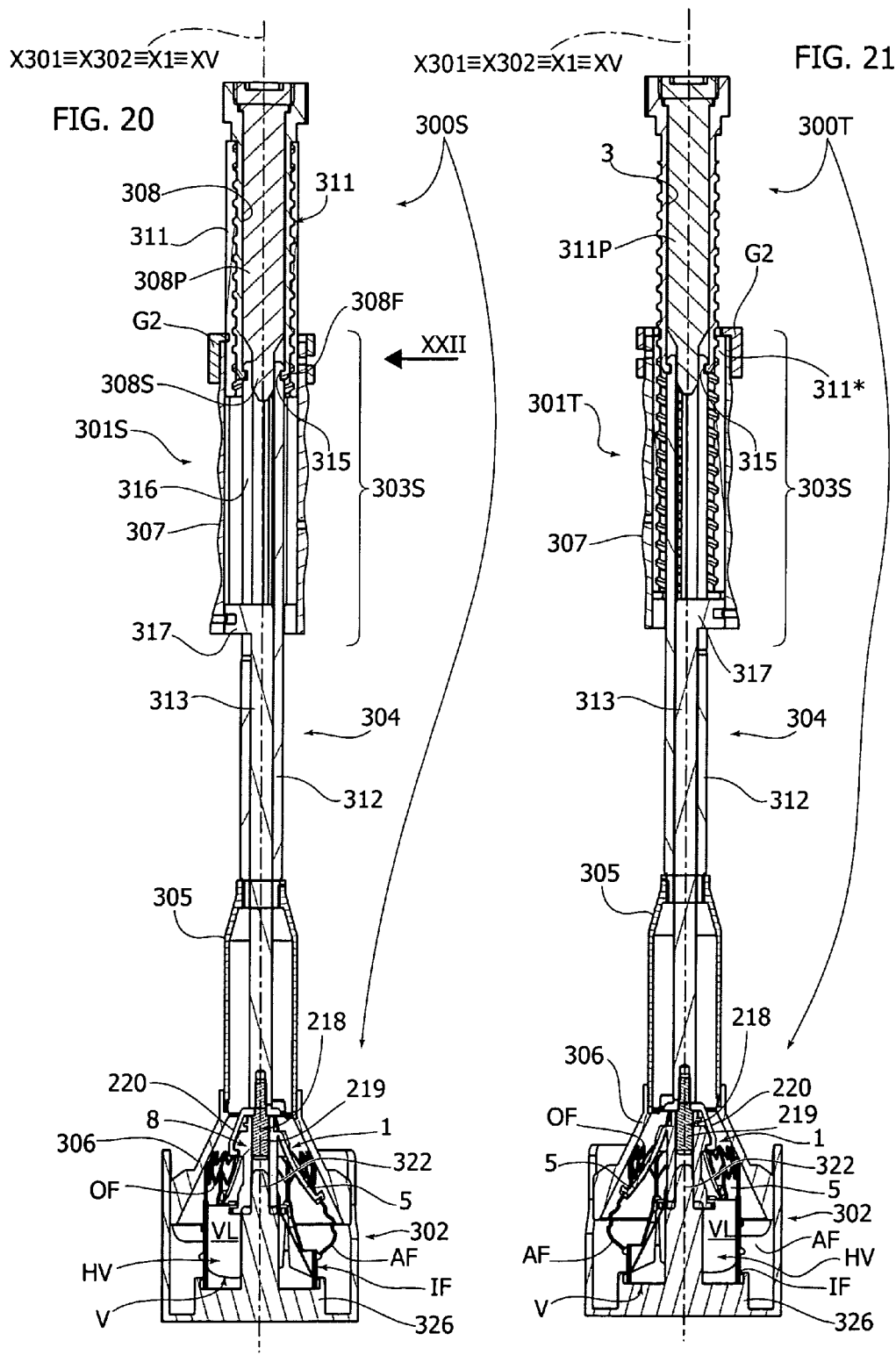

HOLDER FOR HEART VALVE PROSTHESES, CORRESPONDING STORAGE ARRANGEMENT, DELIVERY INSTRUMENT AND KIT

CROSS-REFERENCE TO RELATED APPLICATION

This application is a continuation of International Application No. PCT/IB2014/064804, filed Sep. 24, 2014, which is herein incorporated by reference in its entirety.

TECHNICAL FIELD

The present disclosure relates to heart valve prostheses. One or more embodiments may relate to holders, storage arrangements, delivery instruments and/or kits for use with heart valve prostheses.

BACKGROUND

Biological heart valve prostheses are increasingly adopted due to their higher compatibility with the human heart and due to their behaviour being akin to the behaviour of a native heart valve.

Such prosthetic heart valves may be of the expandable type, e.g. with a plurality of coapting valve leaflets of an animal tissue (for instance, bovine or porcine pericardium) coupled with an armature including e.g. a mesh-like structure (for instance a stent structure) of e.g. an elastic or superelastic material such as Nitinol.

Such heart valve prostheses may be delivered to the implantation site in a collapsed condition, that is in a condition radially contracted to reduced dimensions.

Collapsing the valve onto a delivery tool may involve "crimping" (i.e. radially collapsing) the valve and coupling it with a delivery instrument, this being likely to be a delicate stage of the heart valve replacement intervention.

An expandable prosthetic biological heart valve may be stored in a storage (e.g. sterile) solution within a storage container ("jar"), which may be opened only just before the crimping operation. Opening the container and placing the valve into a crimping tool for crimping the valve onto the delivery instrument may imply manipulation of the valve prosthesis by an operator in order to handle, angularly orient, axially position and eventually crimp the valve onto the delivery tool, without in any way affecting the integrity of the prosthesis.

Document US-A-2009/0054976 discloses an exemplary loading tool for withdrawing, crimping and loading a stent mounted valve into a delivery catheter and for pushing the stent mounted valve from the delivery catheter into a native heart valve orifice.

One or more embodiments herein aim at providing an improved arrangement for holding a valve prosthesis, optionally in a storage container and/or in a delivery instrument or kit.

SUMMARY

Exemplary embodiments herein may refer to a holder for heart valve prostheses, the holder including:
a hub portion having a longitudinal axis,
an engagement portion coupled to the hub portion (2) and including a plurality of finger members variably positionable relative to the hub portion between a collapsed condition wherein the finger members are closed onto the hub portion and an expanded condition wherein the finger members radially protrude with respect to the hub portion for engaging a heart valve prosthesis, wherein the finger members are L-shaped.

Exemplary embodiments herein may also relate to a heart valve prosthesis storage arrangement including:
a container with a filling of a storage solution for heart valve prostheses,
an expandable heart valve prosthesis having an armature, the expandable heart valve prosthesis being held within the container with a filling of a storage solution by means of a holder according to any of the embodiments exemplified herein, wherein the holder is in the expanded condition and the heart valve prosthesis is supported within the container by the armature of the heart valve prosthesis resting on the distal ends of the finger members of the holder.

Exemplary embodiments herein may also relate to a delivery instrument for expandable heart valve prostheses, wherein:
the delivery instrument includes a handle, a shaft, and a delivery sheath displaceable along a longitudinal axis of the delivery instrument,
the shaft includes a connector member and a funnel shaped member coupled to the delivery sheath, the connector member coupleable to a holder according to any of the embodiments exemplified herein with a heart valve prosthesis coupled thereto, with the delivery sheath in a fully retracted position,
the delivery sheath is displaceable axially towards a fully advanced position, whereby the relative movement between the funnel shaped member and the heart valve prosthesis coupled to the holder results in a radial contraction of the heart valve prosthesis and loading of the same into the delivery sheath.

Exemplary embodiments herein may also relate to a kit for crimping, loading and delivering expandable heart valve prostheses, the kit including:
a storage arrangement according to any of the embodiments exemplified herein,
a loading fixture configured to mate with the holder with the heart valve prosthesis coupled thereto, and
a delivery instrument,
wherein the delivery instrument includes a handle, a shaft, and a delivery sheath displaceable along a longitudinal axis of the delivery instrument,
wherein the shaft includes a connector member configured for mating with the holder and a funnel shaped member coupled to the delivery sheath, and
further wherein:
the delivery instrument is configured to mate with the holder, already mating with the loading fixture, with the delivery sheath in a fully retracted position,
when the delivery sheath is displaced axially towards a fully advanced position, the relative movement between the funnel shaped member and the heart valve prosthesis coupled to the holder results in a radial contraction of the heart valve prosthesis and loading of the same into the delivery sheath.

While multiple embodiments are disclosed, still other embodiments will become apparent to those skilled in the art from the following detailed description, which shows and describes illustrative embodiments.

Accordingly, the drawings and detailed description are to be regarded as illustrative in nature and not restrictive.

The appended claims are part of the technical disclosure herein provided in relation to the embodiments.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIGS. 20 to 24 illustrate further embodiments of the delivery instrument of FIG. 7, with FIG. 22 illustrating a detail according to pointer XXII in FIG. 20 and FIG. 23 showing a sectional view taken along line XXIII-XXIII of FIG. 22.

Figure 1:
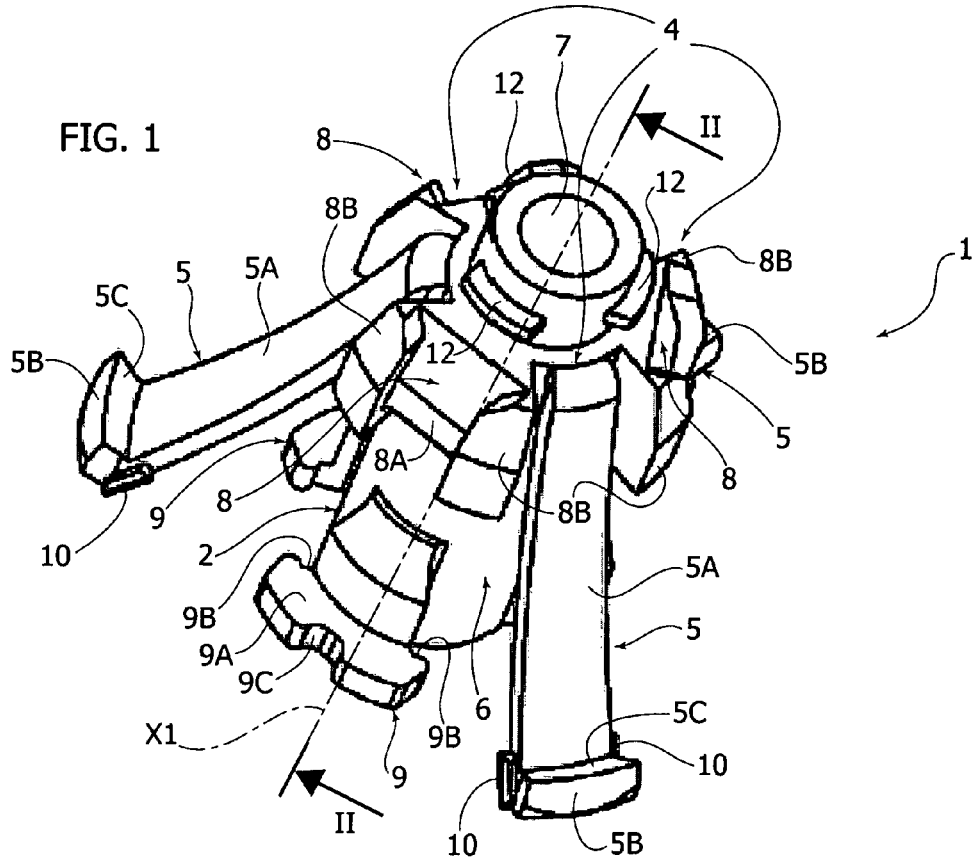
FIG. 1 is a perspective view of a holder for heart valve prostheses according to various embodiments.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

In the following description, numerous specific details are given to provide a thorough understanding of examples of embodiments. The embodiments can be practiced without one or more of the specific details, or with other methods, components, materials, etc. Reference throughout this specification to "one embodiment," "an embodiment," "exemplary embodiment," or "various embodiments" means that a particular feature, structure, or characteristic described in connection with the embodiment is included in at least one embodiment. Thus, the use of these phrases throughout this specification is not necessarily intended to refer to the same embodiment. Furthermore, the particular features, structures, or characteristics may be combined in any suitable manner in one or more embodiments.

It was observed that a number of factors may play a role in operation of a holder for heart valve prostheses.

For instance, the assembly of such a holder and a heart valve prosthesis mounted thereon may be hyperstatic (i.e. constrained), which increases the risk of undesired stresses being applied to the valve prosthesis.

Also, a holder (e.g. for use in a loading tool) may not be readily adapted to existing designs of valve prostheses, so that geometric features/modifications in the structure of the valve prosthesis may be required in order to match those on the distal ends (prong tips) thereof, i.e. the heart valve prosthesis must be re-designed in order to be able to engage the loading tool properly.

In arrangements as disclosed e.g. in US-A-2009/0054976, the geometric features provided on the heart valve prostheses to mate with the loading tool may include webs or tabs protruding with respect to the valve armature, possibly including right angle edges or similar structures likely increasing the risk of damage to the walls of the blood vessel contacted by the heart valve prosthesis once implanted in the human heart (e.g. by damaging the aortic tunica intima in the case of an aortic valve prosthesis implantation).

Figure 2:
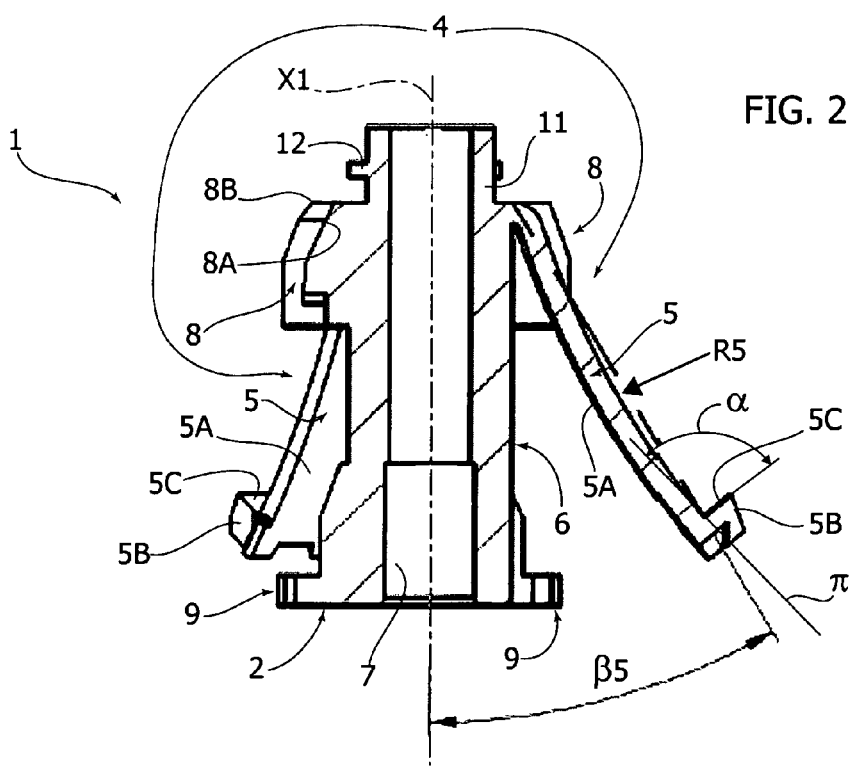
FIG. 2 is a sectional view along the line II-II of FIG. 1.

In FIGS. 1 and 2, reference number 1 indicates as a whole a holder for a heart valve prosthesis. In one or more embodiments, the holder 1 may include a hub portion 2 extending along a longitudinal axis X1 and an engagement portion 4 coupled to the hub portion and including a plurality of finger members 5 variably, positionable relative to the hub portion 2 and the longitudinal axis X1.

In one or more embodiments herein, the finger members may be L-shaped and thus include a first (body) portion 5A primarily extending along a linear direction and a second (distal) portion 5B which forms a distal abutment member to complete the L-shape of the finger member. The distal portion 5B is located at the distal of the respective finger member 5 and exhibits an axial abutment surface 5C.

In one or more embodiments herein, the finger members 5A are provided in the number of three and are angularly spaced by an angle of 120 degrees relative to each other (in other words, they are evenly spaced) around the axis X1. In other embodiments the finger members may be provided in a number higher than three, e.g. four, five, six, nine.

In one or more embodiments herein, the finger members 5 may be integral with the hub portion 2 (for instance by being moulded one-piece therewith by using e.g. a plastics material).

In one or more embodiments herein, the attachment points of the finger members 5 to the hub portion 2 may thus be a so-called "living hinge", which enables variable positioning of the finger members 5 relative to the hub portion 2 and the longitudinal axis X1.

In such embodiments, the living hinge may be sized and dimensioned to provide a certain degree of resiliency which tends to bias the associated finger member radially outwards as shown in FIG. 1. In that way, the finger members 5 may be resiliently hinged to the hub portion 2.

In other embodiments, the finger members 5 may be pivotally connected to the hub portion 2 and may include a resilient member to bias the respective finger member 5 outwards as shown in FIG. 1, thereby replacing the action of the living hinge at the attachment point thereof.

As seen e.g. in FIG. 2, in various embodiments the finger members 5 the first portion 5A may extend primarily along a linear direction.

In one or more embodiments herein, the linear direction may be rectilinear or may exhibit a curvature in a radial plane of the holder 1. In one or more embodiments herein, the first portion 5A may have a curvature defined by a radius R5 and such as to define a concave outer surface and a convex inner surface, wherein the outer surface of the finger members 5 is that facing the outside of the holder, while the inner surface is that facing the hub portion 2.

Optionally, such curvature may result in an angle α, defined between the abutment surface 5C of the second portion 5B and a plane π tangent to the outer surface of the first portion 5A at the interface of the second portion 5B, being greater than 90 degrees. In various embodiments such angle may fall in the range 70 to 110 degrees.

In one or more embodiments herein, the finger members 5 may be biased outwards either by the action of a "living hinge" at the connection point between the hub portion 2 and the finger member 5 itself, or by the action of a resilient biasing member.

In one or more embodiments herein, in an undeformed condition of the holder 1 the finger members 5 protrude radially outwardly, thus defining a first, expanded, condition of the holder 1 wherein the finger members are arranged radially protruding with respect to the hub portion 2. In one or more embodiments, the finger members may be arranged at an angle β5 with respect to the longitudinal axis X1 ranging from 20 to 40 degrees.

In one or more embodiments, the hub portion 2 may include a cylindrical body 6 having an axial through hole 7 and including a plurality of radially protruding formations arranged at various axial positions along the longitudinal axis X1.

In one or more embodiments, the cylindrical body 6 may include a first set of e.g. three radially protruding proximal formations 8 spaced apart by 120 degrees, and a second set of e.g. three radially protruding distal formations 9 spaced apart by 120 degrees, wherein the terms "proximal" and "distal" are herein used with the reference to the attachment points of the finger members 5 to the hub portion 2 (and the cylindrical body 6), so that a proximal position is a position in proximity of the attachment points.

In such embodiments, the formations 8 and 9 may be arranged at opposite axial ends of the cylindrical body 6.

For instance, in one or more embodiments;
the proximal formation 8 may include a central recessed portion labelled as 8A, with e.g. two side portions 8B protruding therefrom in the radial direction; and
the distal formation 9 may be configured as a radial web or tab exhibiting an axial abutment surface 9A and a pair of lateral recesses 9B located on opposite sides of each formation 9 and configured for a snap-fit engagement with corresponding tangential protrusions 10 located on opposite sides of the finger members 5.

Optionally, in one or more embodiments, the distal formations 9 may be further provided with a notch 9C located substantially in a central position thereof.

in one or more embodiments, the provision of the recesses 9B and the protrusion 10 allows the maintenance of the collapsed configuration of the holder 1 so that, with the finger members 5 are biased inwardly and closed onto the hub portion 2, a snap-fit engagement may take place between the recesses 9B and the protrusions 10 thus retaining the finger members 5 closed onto the hub portion 2.

In one or more embodiments, the holder 1 may be so arranged that there is an alternation between finger members and axial pairs of radially protruding formation of the hub portion.

In one or more embodiments, in the closed condition of the holder 1, the alternate sequence of distal formations 9 and portions 5B of the finger member 5 may thus defines a crown of axial abutment surfaces which may cooperate in defining a retention fixture for a heart valve prosthesis to be coupled to the holder 1.

In one or more embodiments the hub portion 2 may include a (proximal) terminal collar member 11 having a plurality of radially protruding tabs 12 intended to facilitate the coupling with a support member in a storage container.

Figure 3:
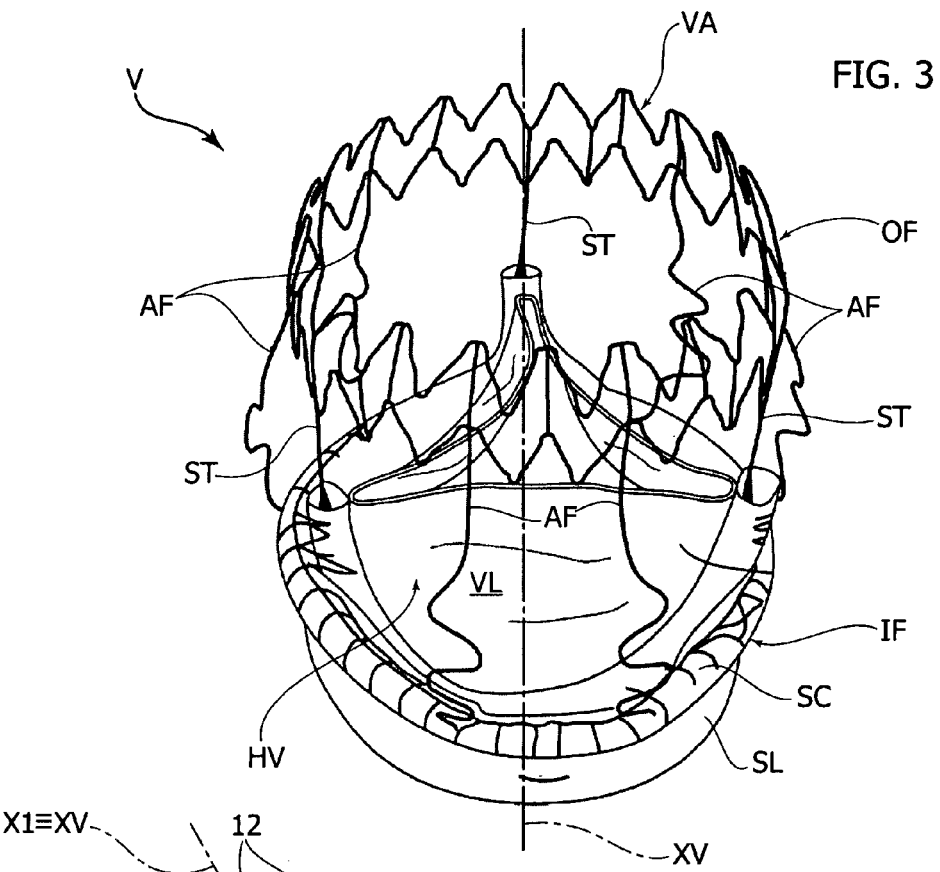
FIG. 3 is a perspective view of an exemplary heart valve prosthesis configured for engaging with the holder of FIGS. 1 and 2.

FIG. 3 shows an exemplary embodiment of a heart valve prosthesis V which may be coupled with one or more embodiments of a holder 1 herein.

Such an exemplary heart valve prosthesis may be as disclosed e.g. in EP 1 690 515 B1 in the name of the same Applicant.

Such a heart valve prosthesis includes a radial expandable valve armature VA coupled to a prosthetic biological heart valve HV including a plurality of coapting valve leaflets VL. The prosthesis V has a main longitudinal axis XV. The valve armature VA includes an inflow ring IF and an outflow ring OF. In the embodiment illustrated in the figures, the inflow ring and the outflow ring IF, OF, are bridged by three longitudinal struts ST which act as supporting and anchoring (fixing) members for the prosthetic valve HV and which extend according to a general rectilinear trajectory, and by three pairs of outwardly protruding anchoring formations AF which are configured for the accommodation within the sinuses of Valsalva of a patient: the prosthesis V represented in the figures is in fact an aortic valve prosthesis. The three pairs of anchoring formations AF are angularly spaced by 120 degrees around the longitudinal axis XV of the heart valve prosthesis V, with the same angular distribution being applied to the longitudinal studs ST which are also evenly spaced with respect to adjacent pairs of anchoring formations AF. Each of the inflow ring IF and outflow ring OF are configured as a mesh-like structure which is designed to experience radial expansion and contraction and which is essentially configured as a stent structure. The inflow ring IF may be covered by a sealing member SL and a sewing cuff SC, while the outflow ring OF is in general free from covering structures and may have an inwardly flared geometry so as to avoid damages to the aortic tunica intima. An example of such an inwardly flared geometry is disclosed for example in EP 2 119 417 B1 in the name of the same Applicant.

It is to be noted that the terms "proximal" and "distal" used in relation to the heart valve prosthesis V reflect the direction of blood flow within the prosthesis so that the inflow ring is a proximal ring while the outflow ring is a distal ring, with the same rationale applying to any sub-structure of the valve V.

Figure 4:
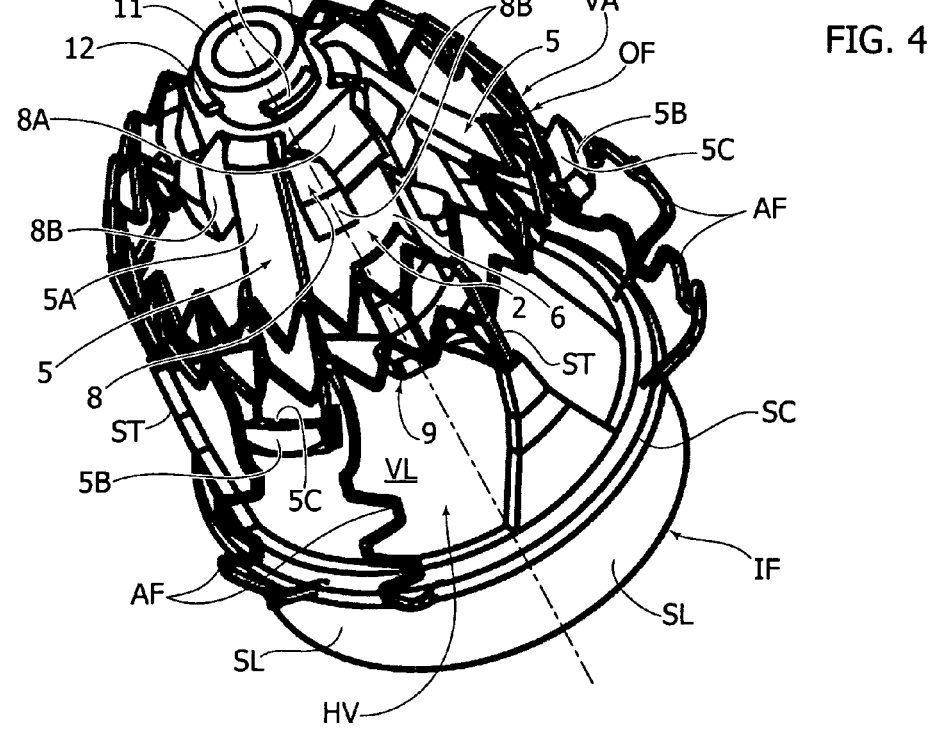
FIG. 4 is a perspective view of the valve of FIG. 3 engaged with the holder of FIGS. 1 and 2.

FIG. 4 is exemplary of the engagement between a holder 1 of one or more embodiments herein and the heart valve prosthesis B, with the holder 1 maintained in the expanded condition with the finger member 5 protruding radially outwardly from the hub portion 2.

As visible in FIG. 4, engagement may occur by arranging the finger members at locations corresponding to the pairs of anchoring formations AF, e.g. with finger members located between the adjacent anchoring formations AF of each pair.

In one or more embodiments, engagement may occur by abutment of a proximal peripheral edge of e.g. the outflow ring (for instance the edge of the outflow ring facing the sewing cuff SC) of the heart valve prosthesis against the distal ends of the finger members 5, with the portions 5B providing abutment surfaces 5C are located.

In one or more embodiments, the heart valve prosthesis may thus be supported by the holder (e.g. within the container to be described in the following) by the armature (e.g.

VA) of the heart valve prosthesis resting (at the surfaces 5C) on the distal ends of the finger members 5 of the holder 1.

In one or more embodiments, such a support action may thus be a gentle, unconstrained (i.e. non-hyperstatic) support action which minimizes the risk of undesired stresses being applied to the valve prosthesis.

Also, in one or more embodiments, such a support action may be achieved without any changes the structure of the valve prosthesis, that is the holder of one or more embodiments herein lends itself to be coupled with such a heart valve prosthesis without any adaptations/modifications of the prosthesis.

In one or more embodiments, upon engagement of the holder 1 and the heart valve prosthesis V, the holder 1 may exert a self-centering action by means of biasing forces developed by the finger members 5. Such centering action may facilitate alignment of the longitudinal axis XV of the valve V and the holder 1, so that the holder 1 and the valve V are coaxial to each other.

In one or more embodiments, the relative axial position between the holder 1 and the valve V may not be determined solely by engagement of the holder 1 with the valve V.

As noted, abutment between the distal ends of finger members 5 and the outflow ring OF of the prosthesis V is intended to avoid axial constraints which prevent the relative movement in both directions along the longitudinal axis X1 of the holder 1 and the valve prosthesis V. In fact, since the valve prosthesis V (e.g. outflow ring OF) merely abuts against (i.e. rests on) the distal ends of the finger members 5, relative movement of the holder 1 and the heart valve prosthesis V along the longitudinal axis X1 of the holder is still permitted in the directions of "lifting" the valve prosthesis V with respect to the surfaces 5C of the finger members 5.

Stated otherwise, when the outflow ring OF of the valve prosthesis V is in contact with (i.e. rests on) the abutment surfaces 5C of the finger members 5, the possibility would exist of e.g. pushing the holder 1 down through the prosthesis V. Conversely, pulling the holder 1 outwardly away from the prosthesis V in an axial direction (i.e. in an inflow-to-outflow direction) will be prevented on account of the abutment between the outflow ring OF and the surfaces 5C.

Figure 5:
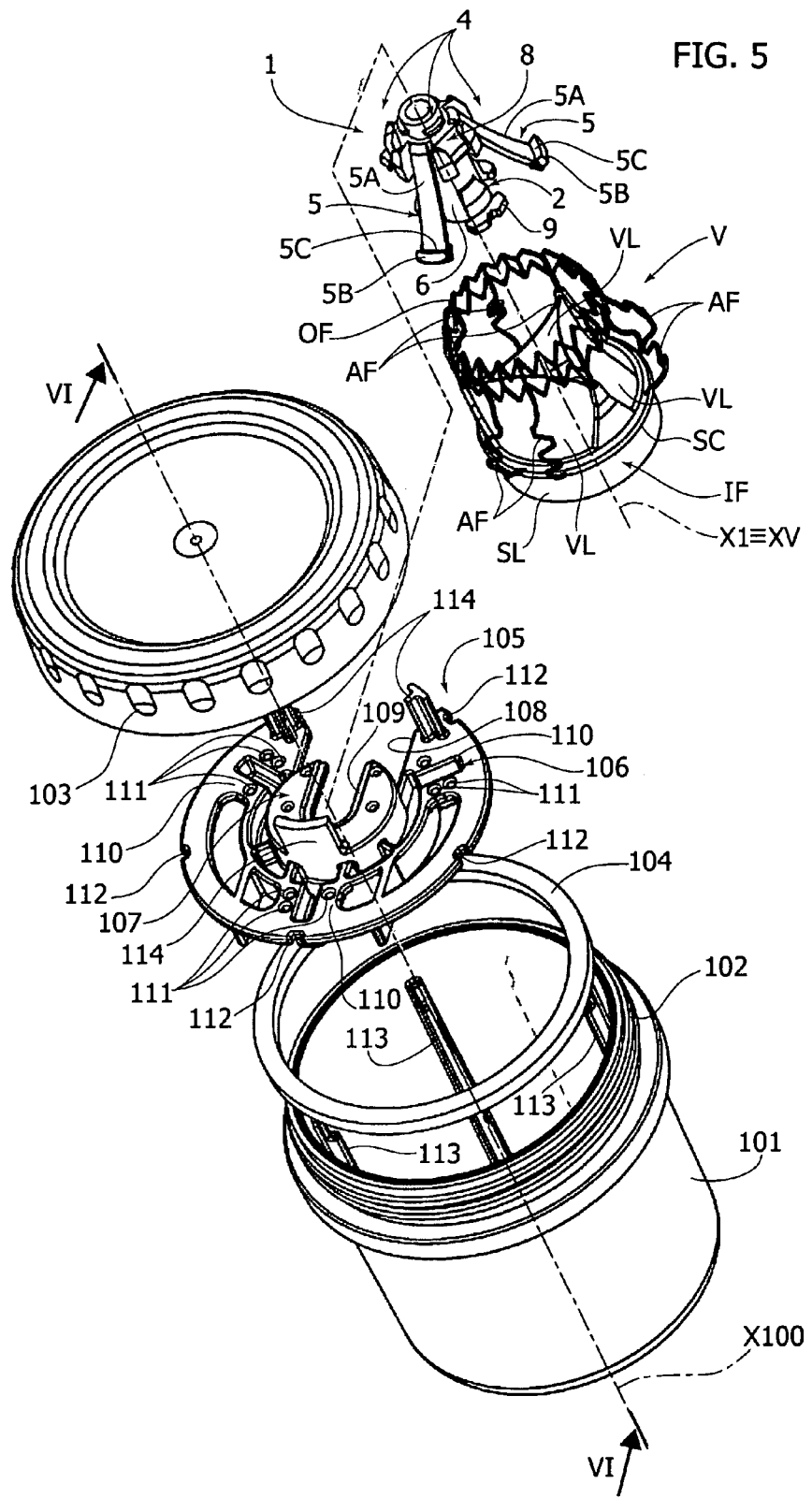
FIG. 5 is an exploded perspective view of a storage container according to various embodiments.
Figure 6:
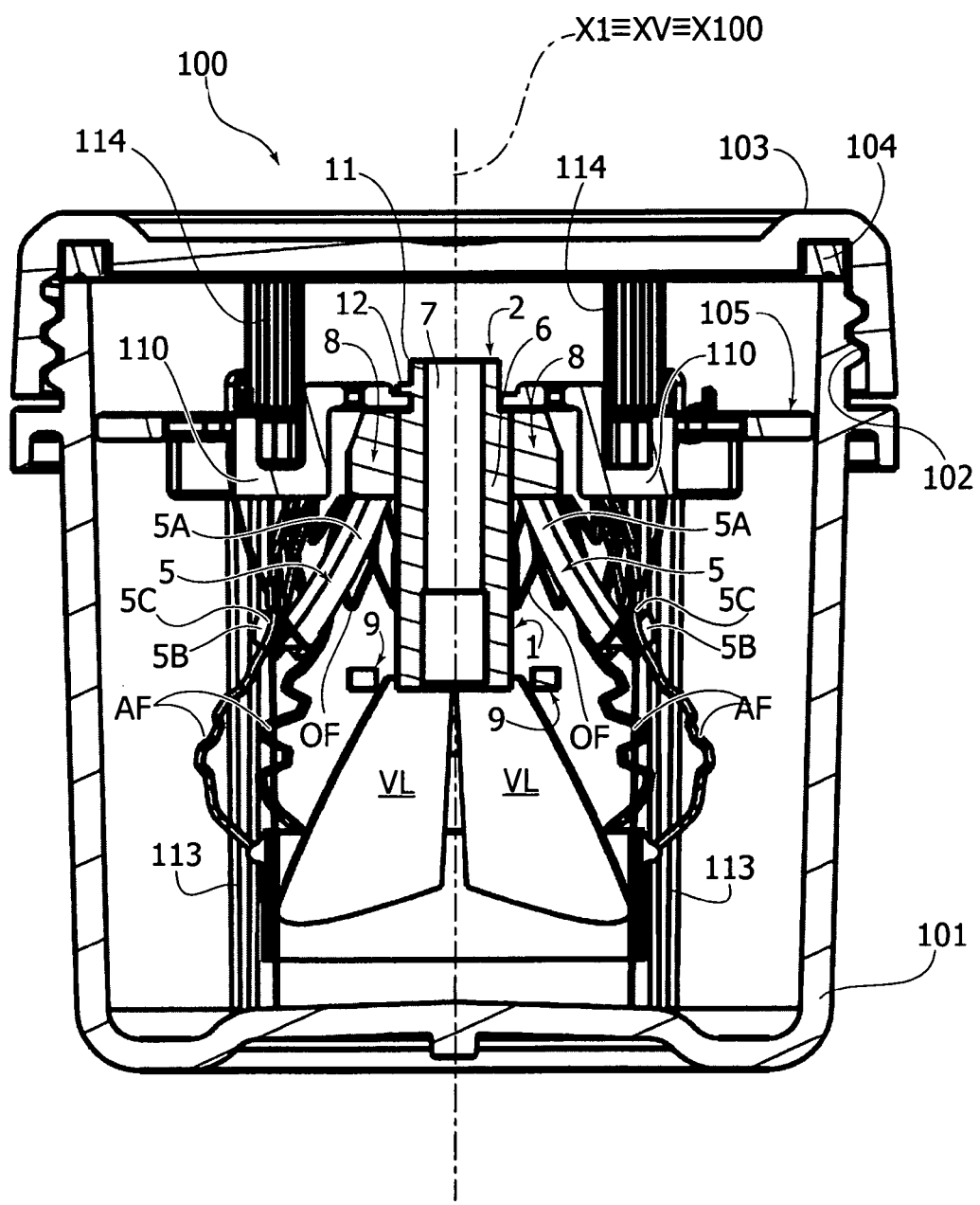
FIG. 6 is a sectional view in the assembled condition of the storage container of FIG. 5 and taken along the line VI-VI of FIG. 5, FIG. 7 includes a first portion labelled as FIG. 7A showing a delivery instrument configured for cooperating the holder and the heart valve prosthesis of the proceeding figures, and a second portion labelled FIG. 7B which illustrates an exemplary loading fixture of the delivery instrument of FIG. 7A.

FIGS. 5 and 6 exemplify embodiments of a storage arrangement (package) for a heart valve prosthesis.

In one or more embodiments herein, a storage arrangement 100 may include a container ("jar") 101 having a e.g. threaded collar 102 for engagement by a closure cap 103, optionally with the interposition of a sealing ring 104 to make the container fluidly sealed.

In one or more embodiments herein, the container 101 may receive a filling of a storage solution for the valve prosthesis V. A sterile solution such as a saline solution is exemplary of such a storage solution.

In one or more embodiments herein, the storage arrangement may include a support member 105 to which the assembly of the holder 1 with the valve prosthesis V mounted thereon may be coupled. In one or more embodiments, the support member 105 may include a disk-shaped element with an outer flange 106 and a hub 107. In various embodiments, the outer flange 106 and the hub 107 may include e.g. mutually aligned radially oriented recesses 108 and 109, respectively, adapted to define a passage for the insertion of the holder 1 and the valve prosthesis V during coupling with the support member 105.

In one or more embodiments, the recess 109 on the hub 107 may be configured for coupling with the radial tabs 12 on the collar 7 so that the walls of the recess 109 may be forced between the tabs 12 and the proximal formations 8 of the holder 1.

In one or more embodiments, the outer flange 106 may be connected to the hub 107 by means of spoke members 110 where apertures such as axial holes 111 may be provided to pass a suture thread TH. Such suture threads act as retention means adapted to anchor the valve prosthesis V to the support member 105. Such suture threads may be passed through the outflow ring of the prosthesis and then routed through the axial holes 111, thus avoiding undesired displacement between the valve prosthesis V and the holder 1: the suture threads may thus act as retention means adapted to restrain "lifting" of the heart valve prosthesis V away from the distal ends of the finger members 5 of the holder 1 and also adapted to keep the valve in position during transportation.

In one or more embodiments, the periphery of the outer flange 106 may include a plurality of notches 112 configured for slidably cooperating with axial guides 113 provided on the inner surface of the jar 101.

In one or more embodiments, the components of the storage arrangement 100 may be coaxial with a longitudinal axis X100, which may coincide with the axes X1 and XV when the assembly of the holder 1 and the prosthetic valve V housed within the jar 101.

An example of this arrangement is shown in FIG. 6.

In one or more embodiments, the support member 105 may be further provided with axial protrusions 114 configured to act as spacer elements with respect to the cap 103. In such embodiments, the longitudinal guides 113 may be provided with a stop member limiting the axial displacement of the support member 105 within the jar 101. Firm and stable axial positioning of the support member 105 (and, consequently of the entire assembly with the holder 1 and the valve V) can thus be achieved.

In FIGS. 7A and 7B reference number 200 designates as a whole a crimping, loading and delivery system for a heart valve prosthesis V.

In one or more embodiments, the system 200 may include a delivery instrument 201 and a loading fixture 202.

In such embodiments, the delivery instrument 201 may in turn includes a handle 203, a shaft 204, a delivery sheath 205 coupled to the shaft 204 and a funnel-shaped member 206 configured as a sleeve member having a conical inner surface, optionally having a frusto-conical geometry overall.

Figure 8:
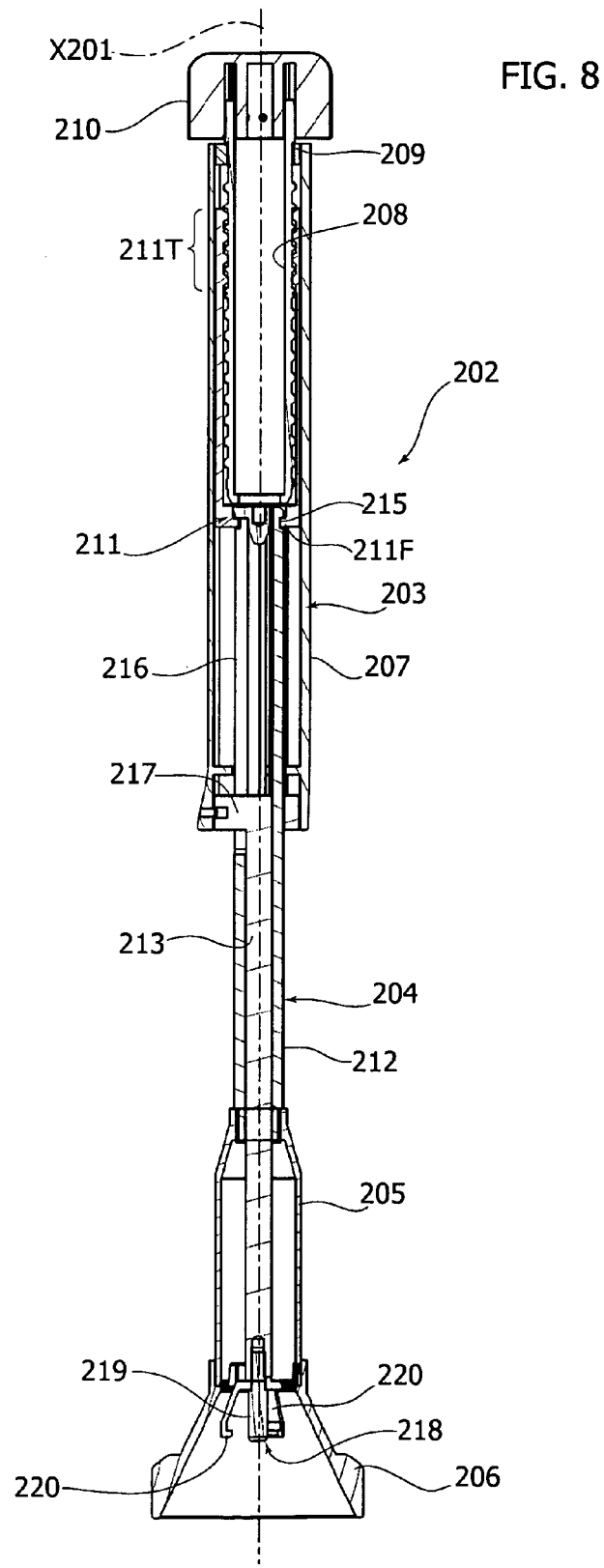
FIG. 8 is a sectional view taken along line VIII-VIII of FIG. 7A, FIGS. 9 to 19 are exemplary of a valve loading and delivery sequence according to various exemplary embodiments.

As shown e.g. in FIG. 8, the handle 203 may include an outer tubular member 207 having an outer surface. In one or more embodiments this may be provided with geometric features intended to improve the grip by the hand of a practitioner and/or may house a mechanism permitting the delivery sheath 205 to be displaced along a longitudinal axis X201 of the delivery instrument 201.

In one or more embodiments, that mechanism may include a screw 208 rotatably supported by a bushing 209 with respect to the tubular member 207. The screw 108 may be further connected in rotation to a rotary knob 210 by means of which the screw 208 can be rotatably actuated.

In one or more embodiments, the screw 208 may have an outer thread engaging an inner thread 211T of a slide member 211; the slide member 211 may be a tubular member having the inner thread 211T on an inner surface thereof an a terminal inner flange 211F.

In one or more embodiments, the slide member 211 may be axially movable along the axis X201 and prevented from rotating about that axis e.g. by means of a grub screw engaged in an axial groove provided on an outer surface thereof.

In one or more embodiments, the shaft 204 may include a hollow outer member 212 which is slidable along the axis X201 and a core member 213 which is fixed to the tubular member 207 of the handle 203, e.g. with the core member 213 enabled neither to rotate, nor to slide along the axis X201. In some embodiments, the core member 213 and the tubular member 207 may be made in a single piece.

In one or more embodiments, the outer tubular member 212 may include an annular end groove 215 configured for mating with the inner flange 211F of the slide member 211; in that way, the upper tubular member 204 may be enabled to slide (axially) along the axis X201 together with the slide member 211 and over the core member 213. Furthermore, axial rotation of the hollow outer member 212 may be prevented by means of an axial opening 216 into which a stud 217 engages having a radial orientation and made one-piece with the core member 213; the same stud 217 may also serve as a fixing post for connection of the core member 213 and the tubular member 207.

In one or more embodiments, the delivery sheath 205 may be fixed to the outer tubular member 212 of the shaft 204, so that the delivery sheath 205 has the same degrees of freedom (and mechanical constraint), that is, the delivery sheath 205 is capable of sliding back and forth along the axis X201 over the portion of the core member 213 surrounded thereby, while being unable to rotate around the axis X201. In some embodiments, the slide member 211, the outer tubular member 212 and the delivery sheath 205 may be made in a single piece.

In one or more embodiments, the funnel shaped member 206 may be fixed to the delivery sheath 205, thus sharing the same degrees of freedom and constraints of the delivery sheath 205 itself: that is, the funnel shaped member 206 is able to move axially in the direction of the axis X201 but unable to rotate thereabout. However, embodiments are also envisaged wherein the funnel shaped member 206 is coupled to the delivery sheath 205 in a freely rotatable fashion, i.e. with no rotational constraint.

In one or more embodiments, a connector member 218 may be fixed to the end of the core member 213 located at the delivery sheath 205. The connector member 218 may include a centering pin 219 and a plurality of anchoring members 220, e.g. as three members angularly spaced by 120 degrees, configured to achieve coupling with the valve holder 1 as will be detailed in the following. In one or more embodiments, the anchoring members 220 may include radially protruding prongs which are substantially hook-shaped.

With reference again to FIG. 7, in one or more embodiments the loading fixture 202 may include a cylindrical member 202A with a central stud 221 having a terminal pin 222 which is of size and shape compatible for mating with the axial through hole 7 of the holder 1.

In one or more embodiments, the central stud 221 may be connected to the walls of the cylindrical member of the loading fixture 202 by means of radial spoke-like formations 223.

In one or more embodiments, windows W may be provided in the outer surface of the cylindrical member 202A between groups (pairs) of radial spoke-like formations 223. A resilient finger 224 oriented axially along the outer surface of the cylindrical member 202A may extend across the windows W.

In one or more embodiments, the finger member 224 may include a free end 225 defining a step with respect to the remainder of the finger 224 so as to offer an axial abutment surface. In one or more embodiments, such an axial abutment surface may be oriented at a right angle with respect to the axis 202. Each finger member 224 may furthermore be provided with a rib G1 having a sloping surface.

In one or more embodiments, a total number of three resilient fingers 224 may be provided, mutually spaced by 120 degrees the axis X202. In one or more embodiments, the fingers 224 may be located between pairs of adjacent spoke-like formations 223, angularly evenly spaced with respect to each pair of spoke-like formations 223.

Figure 7:
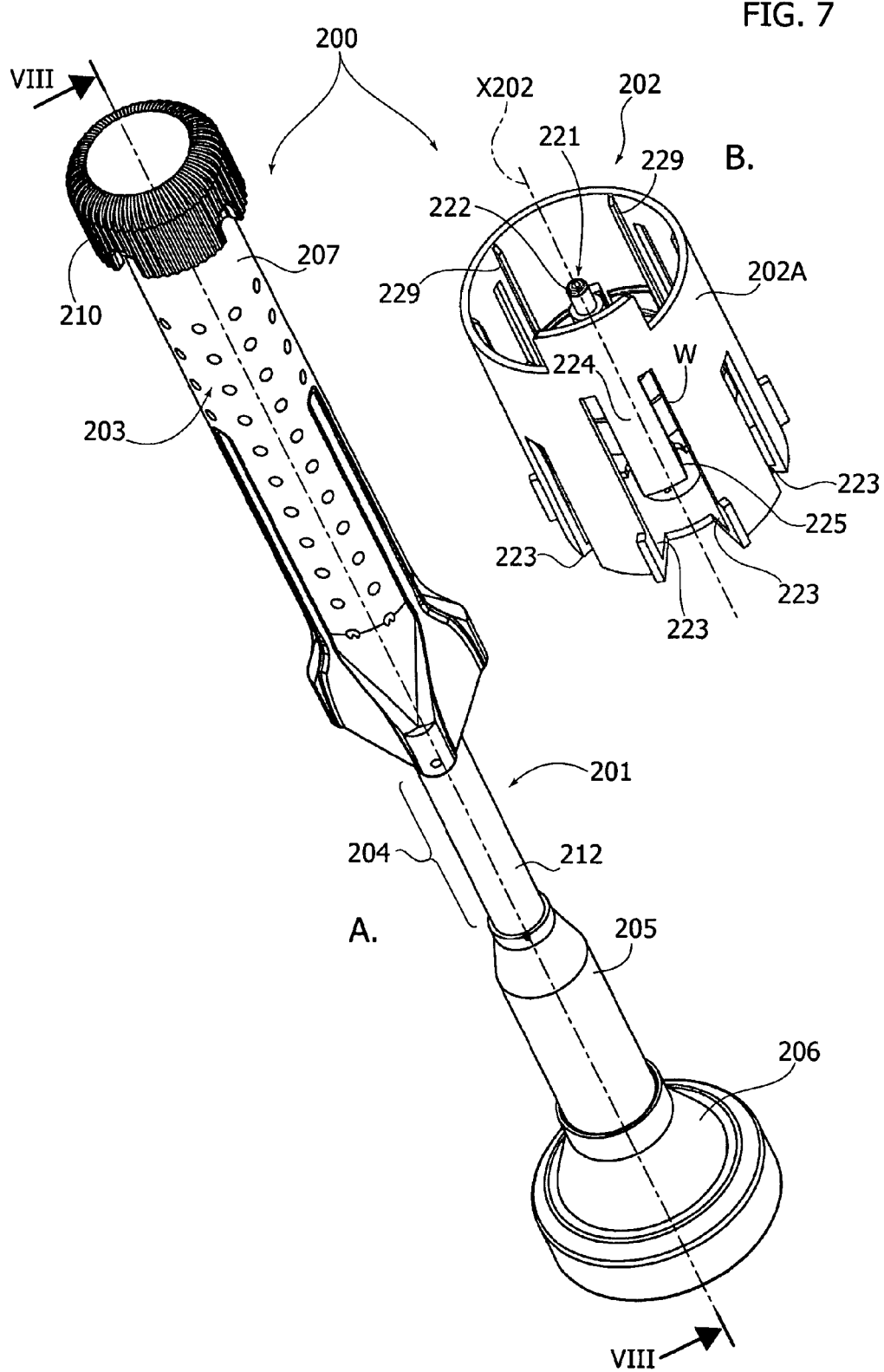

FIGS. 7 and 12 show that, in various embodiments, the fingers 224 may be configured to act as positioning members in the axial direction for a disk shaped member 226, which abuts on the axial abutment surfaces provided by the distal ends 225 by means of a peripheral flange 227. Optionally, similarly to the support member 105, the disk shaped member 226 may include a central hub 228 having a toroidal shape with a central through hole for accommodating the central stud 221.

In various embodiments, in a rest position, the disk shaped member 226 will abut against the distal ends of the resilient fingers 224 in a position lying e.g. at least approximately half-way between the base of the stud 221 and a free end (pin) 222 thereof.

In an arrangement similar to what is provided in the jar 101, in various embodiments the inner surface of the cylindrical member 202A may be provided with longitudinal guides 229 which configured for matching with peripheral features of the disk-shaped member 226 in order to prevent angular rotation thereof. FIGS. 9 to 19 schematically represent an exemplary operational sequence involving the use of the holder 1, the storage arrangement 100 and the loading, crimping and delivery assembly 200.

In one or more embodiments, such an operational sequence may lead to crimping the heart valve prosthesis V and loading it the latter onto the delivery instrument 201 prior to implantation of the valve prosthesis V in a patient's heart.

The exemplary description which follows is provided with reference to an aortic valve prosthesis V, being otherwise understood a substantially similar sequence may be performed also when replacing other native cardiac valves with corresponding expandable prostheses.

In one or more embodiments, a storage arrangement 100 and/or a system 200 may be made available to a practitioner as pre-mounted assemblies ready-to-use in the operational theatre.

Figure 9:
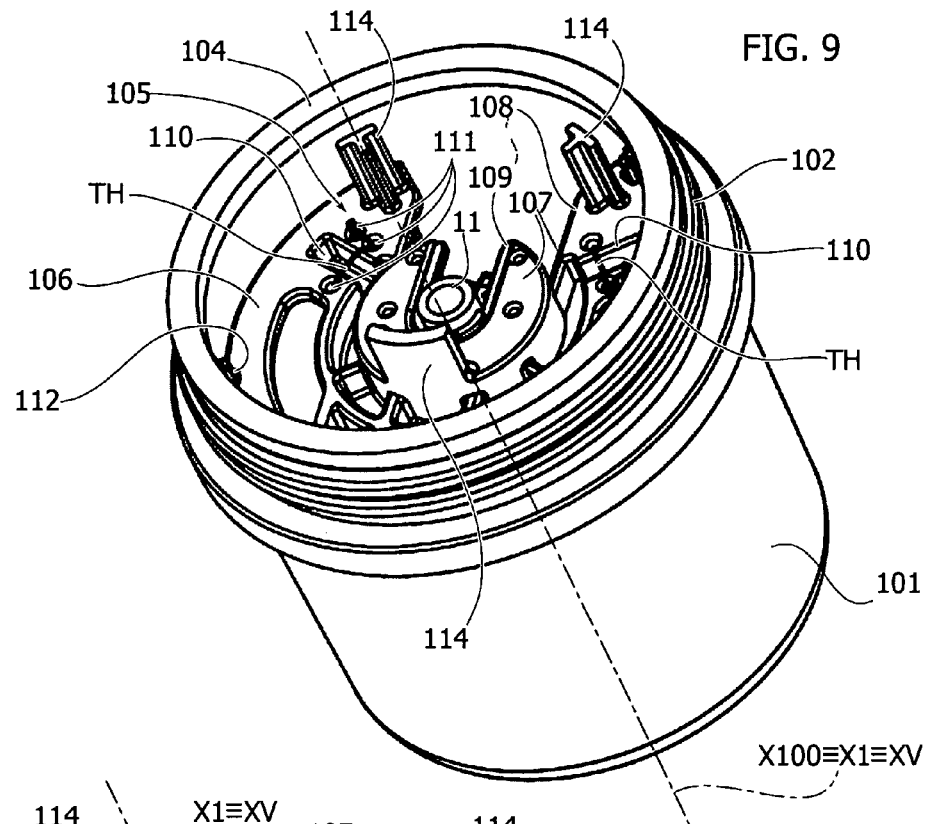

As seen in FIG. 9, as a first step, the storage arrangement 100 will be opened, e.g. by removing the threaded cap 103 from the jar 101. Removal of the cap 109 will give access to the support member 105 which carries the holder 1 engaged within the recess 109. The holder 1 will retain the heart valve immersed within a storage (e.g.) sterile solution contained in the jar 101 with the suture threads TH routed through the holes 111.

The practitioner will then extract the valve prosthesis V from the jar 101. In one or more embodiments this may involve a reduced invasive action e.g. by taking advantage of the spacer members 114 which may also work as gripping members to be grasped by the fingers of the practitioner (or the assistant to the practitioner) to lift the support member 105 and drawing with it the entire assembly including the holder 1 and the heart valve prosthesis V resting on the distal ends of the finger members of the holder 1.

Figure 10:
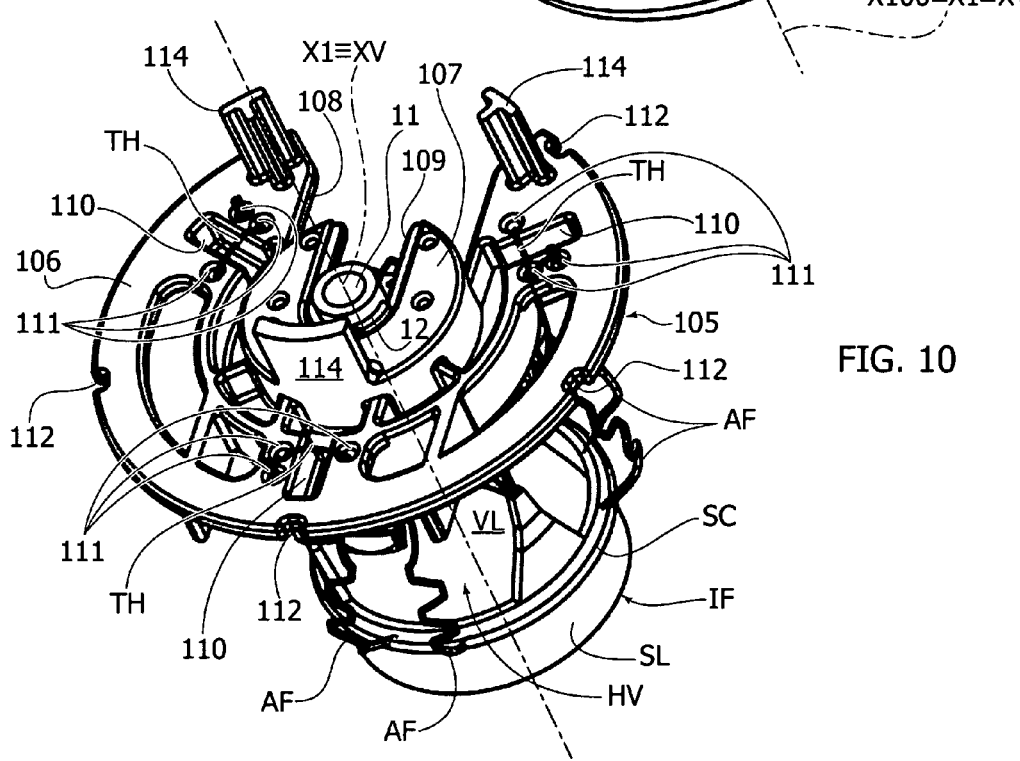

The result of the extraction of the support member 105 is illustrated in FIG. 10, which shows the support member 105, the holder 1 and the heart valve prosthesis V coupled together as described in the foregoing.

The suture treads TH may be still left in place after extraction of the valve V from the jar 101 in order to counter undesired displacement of the heart valve prosthesis V, e.g. in those directions where movement may not be prevented solely by the valve prosthesis resting on the distal ends of the finger members of the holder 1.

Once extracted from the jar 101, the assembly of the support member 105, the holder 1 and the valve prosthesis V may then be coupled to the loading fixture 202 as shown in FIG. 11. To that effect the practitioner (or assistant) may simply mate the holder 1 with the central stud 221, e.g. by coupling the distal pin 222 with a bottom portion of the through hole 7 of the former. In various embodiments, the bottom portion may have a slightly enlarged diameter with respect to the remainder of the hole 7 to generate an annular axial abutment surface which provides an axial position reference for the pin 222.

In one or more embodiments the pin 222 and the bottom portion of the through hole 7 may exhibit a D-shaped cross section, which therefore admits one (and one only) angular positioning, thus ensuring proper angular orientation of the holder 1 with respect the loading fixture 202.

As exemplified in FIG. 11 and FIG. 12, in one or more embodiments, coupling between the holder 1 and the central stud 221 may be carried out with the suture threads TH still in place, thus taking advantage of the ability of positioning of the holder 1 and the valve V by manipulating the support member 105, instead of the holder 1 and/or the valve V.

Once coupling between the holder 1 and the central stud 221 is achieved, the suture threads TH may be cut and removed, so that the support member 105 may be released from the holder 1 by (slightly) sliding it in a radial direction away from the collar 11.

It will be appreciated that in this condition the heart valve prosthesis V will abut against (i.e. rest on) the surfaces 5C of the distal ends 5B of the finger members 5 simply by the action of its weight.

A subsequent step as illustrated in FIG. 13 may envisage positioning the delivery instrument 201 (which includes the funnel shaped member 206 coupled to the delivery sheath 205) coaxially with the assembly of the loading fixture 202 and the holder 1 with the heart valve prosthesis V coupled thereto.

In this condition, the delivery sheath 205 will be in a retracted position, that is in a position of reduced distance with respect to the handle 203, so that the outer tubular member 212 will cover the core member 213 to a reduced extent.

In the retracted position of the sheath 205 (see e.g. FIGS. 13 and 14), the slider member 211 will be arranged substantially at the top portion of the angle 203, in close proximity to the rotary knob 210. The positioning as shown in FIG. 13 is then followed by coupling (mating) the instrument 201 with the holder 1 by means of the connector member 218.

In one or more embodiments, the connector member 218 will couple with the axial through hole 7 by means of the fitting of the pin 219 within the collar 11, while also achieving snap-fit engagement between the fingers 220 and the radially protruding formations 8 of the holder 1. Additionally, in one or more embodiments the pin 219 and the hole 7 may be provided with matching features that allow only a specific angular alignment or a given degree of rotational symmetry, e.g. degree 3.

In one or more embodiments, the difference in radial extension between the side portions 8B and the central portions 8A of the formations 8 of the holder 1 will substantially correspond to the thickness of the anchoring members 220, which are accordingly sized and dimensioned to set between the side portions 8B.

Optionally, in such embodiments, the central and side portions 8A and 8B may have outer surfaces sized and dimensioned to match the outline of the corresponding (mating) anchoring members 220 so that, upon occurrence of snap fit engagement therewith, the anchoring member 220 substantially lies flush with the radially protruding formations 8.

This stage of the operational sequence is shown in FIG. 14, which shows the delivery instrument 201 with the delivery sheath 205 still in the retracted position.

FIG. 15 schematically shows the beginning of a crimping operation of the heart valve prosthesis HV: there, starting from the condition shown in FIG. 14, the practitioner may impart a rotation $\phi$ to the rotary knob 210, thereby controlling a rotation of the screw 208 which ultimately results in an axial translation of the slider 211 along the axis X201. The axial translation of the slide 211 along the axis X201 results in a corresponding axial translation of the outer member 212 along (and over) the core member 213, such translation being indicated by $\Delta x$ in FIG. 15.

The same translation $\Delta x$ will apply to the outer member 212, the delivery sheath 205 and the funnel shaped member 206, while the core member 213 will remains axially fixed and, so to say, defines a core "pillar" of the ensemble which corresponds to the sequence of the stud 221, the holder 1 and the core member 213.

In one or more embodiments, these components may be designed to bear the stresses acting on the assembly along the axis X201 upon actuation of the delivery instrument 201 by the practitioner.

The axial translation $\Delta x$ of the funnel-shaped member 206 will result in a relative movement with respect to the valve prosthesis V coupled to the holder 1. In such relative movement, the valve prosthesis V may e.g. remain in a fixed position without being forced downwards (e.g. dragged) by the funnel shaped member 206 on account of the abutment of the outflow ring OF against the surfaces 5C of the L-shaped finger members 5, and also on account of the presence of the disk shaped member 226, which also provides axial abutment.

The heart valve prosthesis V will thus be a subjected to a drawing (pull) action towards the bottom of the loading fixture 202 (i.e. towards the spoke formations 223). The outer diameter(s) of the assembly made up of the valve prosthesis V and the holder 1 in an expanded condition will thus have to adapt to the (progressively decreasing) inner diameter of the funnel shaped member 206, thus defining an interference condition which enables the transmission of axial forces between the funnel shaped member 206 and the assembly.

Optionally, the L-shaped geometry of the finger members 5 and the simple abutment of the valve prosthesis (e.g. the outflow ring OF) on the surfaces 5C will enable a self-orientation of the heart valve prosthesis V with respect to the holder 1 under, e.g., the action of the funnel shaped member 206 during crimping of the prosthesis V.

In one or more arrangements the deformation of the heart valve prosthesis V may be accommodated without inducing stresses in the structure thereof.

As illustrated in FIG. 15, the relative movement between the funnel shaped member 206 and the heart valve prosthesis V may have a twofold effect, namely:

the armature VA of the heart valve prosthesis V will contract radially on account of the progressively decreasing internal diameter of the funnel shaped member 206 as the funnel shaped member is advanced down through the loading fixture 202, the finger members 5 will close onto the hub portion 2 of the holder 1, again on account of the progressively decreasing diameter of the funnel shaped member 206 as the funnel shaped member is advanced down through the loading fixture 202; by doing so, the holder 1 is brought in its collapsed condition by means of the funnel shaped member 206.

In one or more embodiments, the collapsed (i.e. radially contracted) condition of the holder 1 may be maintained due to the engagement of the protrusions 10 with the formations 9 on the hub portion 2, with the protrusions 10 and the formations 9 brought into engagement by the action of the funnel shaped member 206, that is on account of the progressively decreasing diameter of the funnel shaped member 206 as the funnel shaped member is advanced down through the loading fixture 202.

FIG. 15 also shows that in one or more embodiments, axial advancement of the funnel shaped member 206 together with the delivery sheath 205 will reach a first stop when the funnel shaped member 206 comes into contact with the peripheral flange 227 of the disk shaped member 226.

The provision of the peripheral flange 227 may be intended as a safety measure to allow the practitioner to possibly repeat the sequence of operations described in the foregoing (e.g. when wishing to further refine the (partial) crimping action exerted on the outflow ring OF, the relative positioning of the delivery sheath 205 and the prosthesis V, and/or the relative positioning between the holder 1 and the prosthesis V. In one or more embodiments, the provision of the holder 1 with finger members 5 capable of exerting an axial constraint in one direction only along the longitudinal axis X1 (i.e. the valve prosthesis "rests" on the distal ends of the fingers of the holder 1 and may be "lifted" away therefrom) allows for an easy recovery of the initial condition shown in FIG. 13; that is, the practitioner may easily bring the outflow ring OF back into engagement with the abutment surfaces 5C to restart the collapsing procedure.

Such a "backup" or "repositioning" procedure would be unfeasible in any arrangements providing for a strictly constrained shape coupling between the heart valve prosthesis and the prongs of a holder/loading tool.

The sequence of operations illustrated in FIGS. 9 to 15 may be continued by rotating the rotary knob 210, thereby bringing the delivery sheath 205 (and the funnel shaped member 206) in a (fully) advanced position. In the advanced position the delivery sheath 205 covers (e.g. completely) the valve prosthesis V, while lying at a distance from the handle 203.

Such a condition is visible in FIG. 16.

In one or more embodiments, in the advanced position the slider 211 may reaching a stop member inside the tubular element 207 and with the inner thread 211T engaged on threads of the screw 208 located at a free end thereof. In this condition, the outer member 212 may cover the core member 213 and the delivery sheath 205 may covers the coupling member 219, the holder 1 and the heart valve prosthesis V.

Reaching the stage of FIG. 16 may involve overcoming the axial constraint represented by the abutment surfaces 225 of the fingers 224. In one or more embodiments, this may be achieved due to the resiliency of the fingers 224, which are capable of flexing outwardly of the cylindrical member 202A upon exertion of a sufficient axial force by the funnel shaped member 206 on the ribs G1 by means of the mechanism for actuating the delivery sheath 205. In such embodiments, overriding of the fingers 224 is achieved essentially via the provision of the ribs G1 on the fingers 224. As anticipated, such ribs have a sloping profile which, upon axial contact with the funnel shaped member 206, give rise to a radially outward oriented action on the fingers 224, thereby biasing the latter away from the axis X202.

By doing so, both the funnel shaped member 206 and the disc-shaped member 226 may override the fingers 224 and come to rest on the bottom of the cylindrical member 202A (specifically on the spoke-like member 223) as the rotation of the knob 210 proceeds further.

In one or more embodiments, alignment of the disk shaped member 206 with respect to the loading fixture 202, may be achieved by the member 226 being guided axially by means of the longitudinal guide 229 and, in the final portion of its travel, by a widened cross section of the central stud 211 which substantially matches the inner diameter of the hub 228.

In one or more embodiments, in the condition schematically represented in FIG. 16 the assembly of the coupling member 218 and the holder 1 in the collapsed condition may defines a hub portion of the delivery instrument 201 for engaging the heart valve prosthesis in order to prevent undesired axial movements of the prosthesis while radially collapsed within the delivery sheath. The role and function of such a hub portion may be as disclosed e.g. in European Patent no. EP 1 935 377 B1 in the name of the same Applicant.

Once the condition depicted in FIG. 16 has been reached, the practitioner may then remove the delivery instrument 201 with the heart valve prosthesis loaded and crimped thereinto from the loading fixture 202.

As visible in FIG. 17, the funnel shaped member 206 may be still attached to the delivery sheath 205, and the practitioner may then remove the funnel shaped member 206 by detaching it from the delivery sheath 205, as shown in FIG. 18, without further action on the knob 210 while detaching the funnel shaped member 206.

Figure 19:
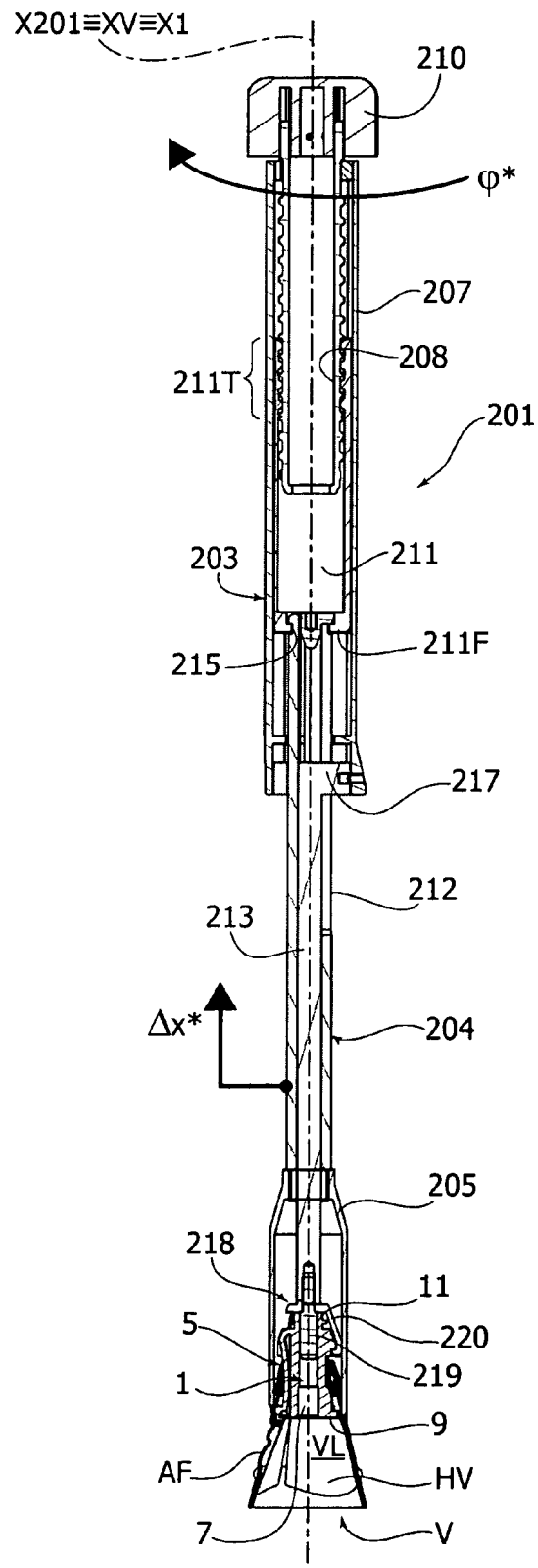

FIG. 19 is exemplary of a delivery instrument 201 during the implantation of the heart valve prosthesis V within the patient's heart.

In one or more embodiments, the heart valve prosthesis V may be deployed at the implantation site, by retracting the sheath 205, e.g. by exerting on the rotary knob 210 an action opposite to the action exerted when crimping and loading the valve V within the delivery sheath 205 in the steps previously described. This will results in the slider 211 being drawn towards the screw 208 and the core member 213, with the holder 1 and the valve V being progressively uncovered.

The action on the rotary knob 210 and the axial movement of the delivery sheath 205 are schematically indicated in FIG. 19 with the references $\phi^*$ and $\Delta x^*$.

The deployment of the heart valve prosthesis V may involve a two-stage procedure.

As a first stage, the inflow portion IF is deployed at the cardiac valve annulus by making sure that proper positioning is reached with respect to the anatomic structure of the patient: FIG. 19 may be regarded as representative of a first stage of the implantation procedure. Note also that at this stage a partial re-collapsing of the valve may still be possible, in order to finely tweak the valve position.

Once the desired orientation and position has been reached, the delivery sheath 205 may be progressively brought to the fully retracted position thereby uncovering the anchoring formations AF and, ultimately, the outflow portions OF. In one or more embodiments, on account of the snap-fit coupling between the L-shaped finger members 5 and the formations 9, the finger members 5 will not step back to the expanded condition upon release of the prosthesis at the implantation site, thereby avoiding damages to the patient's heart on account of undesired and unexpected expansion of the fingers 5. Expansion of the fingers 5 during the implantation of the valve prosthesis V may militate against the possibility of disengaging the holder 1 from the heart valve prosthesis V and at the same time maintaining the positioning of the prosthesis V with respect to the implantation site.

FIGS. 20 and 21 are exemplary of further possible embodiments of a loading, crimping and delivery system for use with a heart valve prosthesis V, e.g. in connection with a loading fixture 302 and a delivery instrument 301.

In the embodiments exemplified in FIGS. 20 and 21 the delivery instrument may include an actuation mechanism of a sliding type (301S) or of the screw type (301T) to indicate the provision of a screw mechanism.

The delivery instruments 301S and 301T otherwise share a same structural configuration, and the actuation mechanism can be varied essentially by changing the relative arrangement between the components thereof. Provided in the following is a detailed description of embodiments of the two delivery instruments and of how the configuration thereof can be varied from the "S" configuration to the "T" configuration.

For instance, the delivery instrument 301S may include a handle 303S, a shaft 204, a delivery sheath 305 coupled to the shaft 304 and a funnel-shaped member 306 which includes a sleeve member having a conical inner surface (e.g. with a frusto-conical geometry overall in some embodiments).

The handle 303S may include an outer tubular member 307 having an outer surface which, in one or more embodiments, may have a wavy appearance to improve the grip by the hand of a practitioner and/or house therein a mechanism which allows the displacement of the delivery sheath 305 along a longitudinal axis X301 of the delivery instrument 301S.

For instance, such a mechanism may include a slider 311 including:
  a screw 308, and
  a threaded sleeve 311* having an inner thread engaging (the whole length of) the threads of the screw 308 so to completely cover the threads of the screw 308.

This coupling results in a barrel having a smooth outer surface. In order to prevent the sleeve 311* from rotating relative to the screw 308, the cross section may in various embodiments be provided with a D-shaped geometry, with a matching cross section given to the cavity inside the tubular element 307.

The shaft 304 may include an outer tubular sheath 312 and a core member 313 arranged within the outer tubular sheath 312. The sheath 312 may include an annular groove 315 at an upper end thereof which is configured to mate with an inner flange 308F of the screw 308. Optionally, in some embodiments a reference pin 308P having a stud 308S may be fitted within the screw 308 so that the stud 308S engages within the outer tubular sheath 312 which is partly housed within the tubular member 307, so as to ensure a firmer anchoring of the sheath 312 to the screw 308.

Similarly to the core member 213, the core member 313, may be neither slidable along, nor rotatable around the axis X301, e.g. is fixed both in translation and in rotation to the handle 303S and more specifically to the tubular member 307.

Similar to the delivery instrument 201, the fixing of the core member 313 to the tubular member 307 may also provide an anti-rotation feature for the outer tubular sheath 312. In one or more embodiments this may include an axial opening 316 adapted to be engaged by a fixing post 317 of the core member 313 engages, thereby defining an axial guide for the outer tubular sheath 312 along the axis X301.

The delivery sheath 305 may be essentially identical to the delivery sheath 205, e.g. may be fixed to the outer tubular sheath 312 and it is therefore slidable therewith but non rotatable around the axis X301.

The connector member 218 previously described may be arranged at a free end of the core member 313 located in correspondence of the delivery sheath 305, One or more embodiments may adopt a loading fixture 302 different from the loading fixture 202, essentially in that it does not include movable parts. For instance, the loading fixture 302 may include a cylindrical body 302A with a longitudinal axis X302 and having a central stud 321 with a pin 322. Similarly to the pin 222, the pin 322 may be configured for mating with the through hole 7 of the holder 1. The base may further include a base 326 wherefrom the stud 321 protrudes.

The sequence of operations already exemplified in connection with FIGS. 9 to 12 is applicable, mutatis mutandis, also to the operation of the delivery system 300.

The assembly including the support member 105, the holder 1 and the heart valve prosthesis V may be extracted from the jar 101 and the holder 1 coupled with the central stud 321 by mating the pin 322 with the axial through hole 7.

Once coupling is achieved, the support member 105 may be removed by cutting the suture threads TH. The delivery instrument 301S may then be positioned coaxial with the axis X301 and coupled with the holder 1 in the manner exemplified in connection with FIGS. 9 to 12.

Crimping of the heart valve prosthesis V and loading of the latter into the delivery instrument 301S may occur by axial displacement along the axis X301 of the slider 311 with respect to the handle 307. This will result in an axial advancement towards the bottom of the loading fixture 302 of the outer tubular sheath 312, the sheath 305 and the funnel shaped member 306, which result in a progressive collapse of the heart valve prosthesis V, with both the holder 1 and the heart valve prosthesis V gently forced into the respective collapsed conditions.

The absence of movable parts in the loading fixture 302 may render it easier to operate and more compact.

Save for the arrangement of the actuation mechanism, the delivery instrument 300T of FIG. 21 is substantially identical to the delivery instrument 300S: parts and components identical or similar to those previously described are designated by the same reference number already adopted for the instrument 301S; a corresponding detailed description will not be repeated in connection with FIG. 21.

In various embodiments the delivery instrument 300T is characterized by the arrangement of the sleeve 311* within the handle 307 wherein it is locked in position by means of a ring nut G2. Note that it is the provision of the ring nut G2 that determines the "S" or the "T" configuration of the actuation mechanism of delivery instrument 300: in the "T" configuration (instrument 300T) the nut G2 may in fact be positioned so as to axially lock the threaded sleeve 311* within the handle 307. Conversely, in the "S" configuration the nut G2 may be positioned so as to allow an axial movement of the sleeve 311* together with the screw 308.

Figure 22:
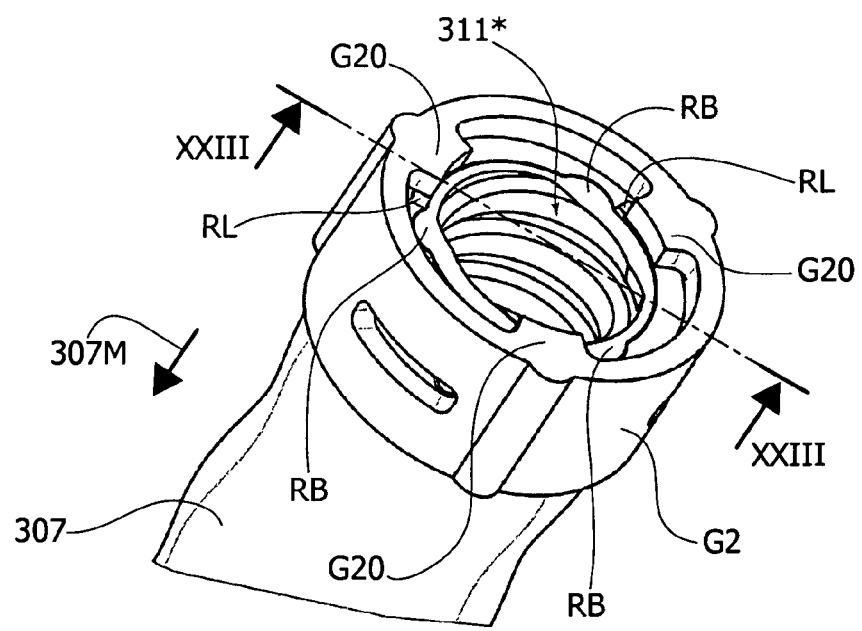
Figure 23:
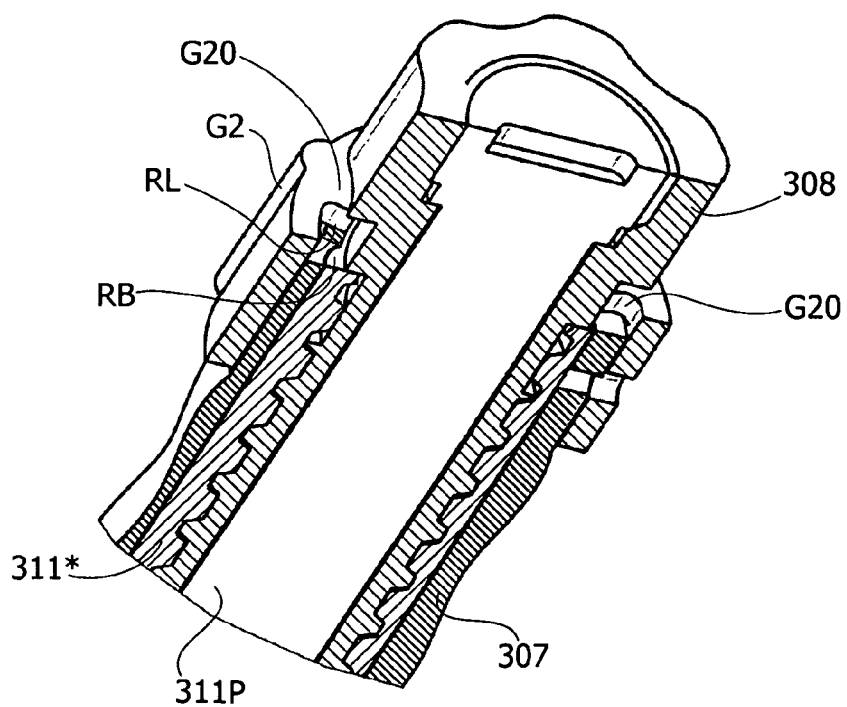

Reference shall be made in this respect to FIGS. 22 and 23: in various embodiments, the threaded sleeve 311* may be provided as a tubular member including three axial ribs RB which protrude radially outwardly, thereby imparting a three-lobed outline to the cross section of the sleeve 311*. Note however that the number of axial ribs RB may vary and in certain embodiments it may be other than three. The axial ribs RB of threaded sleeve 311* may be slidably coupled with corresponding axial grooves on the inner surface of outer tubular member 307. In various embodiments the nut G2 may include a plurality of tabs G20 in a number equal to that of the ribs RB and protruding radially inwardly of the nut G2 itself so that, when the nut G2 is coupled to the outer tubular member 307, the tabs G20 extend over the wall thickness of the outer tubular member 307 at the upper end thereof. Note that in various embodiments the radial length of the tabs G20 is chosen so to be less or equal to the maximum wall thickness of the outer tubular member 307, and at the same time to be greater than the minimum wall thickness of the outer tubular member 307 itself. In such embodiments wherein the outer tubular member 307 is provided with axial grooves, the minimum wall thickness of the outer tubular member 307 is that in correspondence of each axial groove.

In various embodiments, at the upper end of the outer tubular member 307 reliefs RF may be provided which are configured to act as position references for the nut G2. In the position shown in FIGS. 22 and 23, a relative movement of the outer tubular member 307 along the direction 307M and in respect of the sleeve 311* is allowed in so far as the nut G2 is capable of accommodating the overall dimensions of sleeve 311*. The position of the nut G2 therefore corresponds to the "S" configuration: the outer tubular member 307 may slide over the sleeve 311* thereby displacing the delivery sheath 305.

In order to switch to the "T" configuration, in various embodiments the nut G2 may be rotated (for example by overriding the position reference provided by the reliefs RF) so as to overlap the tabs G20 with a corresponding axial rib of the sleeve 311*. In this position, the tabs G20 will overlap both with an axial rib RB and with the axial groove matching therewith, so that a movement of the outer tubular member 307 relative to the sleeve 311* in the direction 307M may not be accomplished: the tabs G2 will prevent the axial separation of the ribs RB and the matching grooves, thereby locking the sleeve 311* in position.

In this condition the handle 303T will thus be able to act as a nut screw having internal threads with which the outer threads of the screw 308 cooperate. Actuation of the sheath 305 along the axis X301 will then occur by actuating in rotation a screw 308 while firmly holding the handle 303T in hand. The screw 308 will then move back and forth (depending upon the direction of rotation imparted thereto) inside the tubular member 307 and the sleeve 311* so that a corresponding back and forth movement along the axis X301 will be transferred to the outer sheath 312 and the delivery sheath 305. It should be noted that in these embodiments a relative rotation occurs between the inner flange 308F and the annular groove 315 on the outer tubular sheath 312, on account on the latter being non rotatable.

Figure 24:
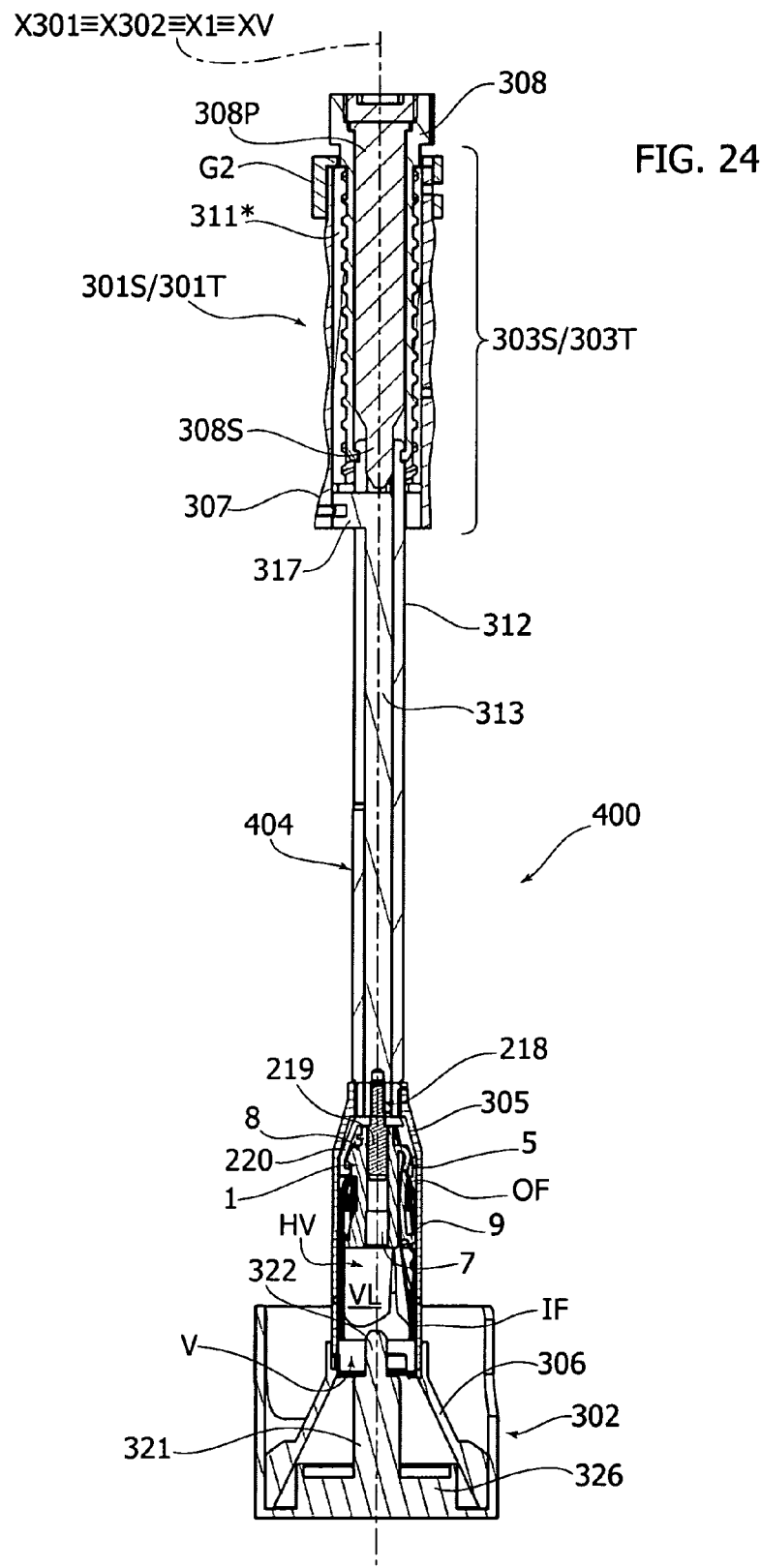

FIG. 24 shows the possible result of the crimping and loading procedure onto the delivery instrument 301 and applies both to the instrument 301S and to the instrument 301T, insofar as the advanced position of the delivery sheath 305 corresponds to the same relative position between the components of the actuation mechanism. The way in which the actuation mechanism brings about the displacement of the sheath 305 along the axis X301 is different from one instrument to the other, as previously described.

After reaching the condition of FIG. 24 the instrument 301S or 301T may be simply removed from the loading fixture 302 and, once the funnel shaped member 306 is removed from the sheath 305, the valve prosthesis V is ready for the implantation within the patient's heart.

In the instrument 301S retraction of the delivery sheath 305 along the axis X301 may be effected by pulling the screw 308 (and the sleeve 311* therewith) distally away from the handle 303S starting from the condition of FIG. 21.

In the instrument 301T the retraction of the sheath 305 may be effected by rotating the screw 308 so as to "unscrew" the latter from the handle 303T.

Expressions such as e.g. "in one (or more) embodiment(s)", "in some embodiments", "in other embodiments", "in various embodiments", and "in further embodiments" have been used throughout the detailed exemplary disclosure of embodiments as provided herein. Such expressions will make it clear that the present disclosure is meant to be exemplary also of embodiments resulting e.g. from applying a feature disclosed in connection with an embodiment exemplified in one of the figures to an embodiment exemplified in another one of the figures;

combining in one embodiment features disclosed separately in connection with plural embodiment exemplified in the figures.

Accordingly, although the present disclosure has been developed with regard to certain specific embodiments, it is to be understood that the disclosure is not meant as a limitation and is intended to cover all the modifications and equivalents falling within the scope of the claims.

For example, while in all the embodiments exemplified in the foregoing the holder 1 supports the heart valve prosthesis V from the inside of the structure thereof (i.e. the holder 1, and particularly the finger members 5, is positioned within the armature VA), in other embodiments the supporting action—albeit still exerted by means of contact between axial abutment surfaces 5C on the finger members 5 and the outflow ring OF (or inflow ring IF in some embodiments)—may be exerted from the outside of the heart valve prosthesis, i.e. with the finger members of the holder 1 being arranged outside of the valve armature.

Additionally, further preferred embodiments include, for example:

Embodiment 1 a holder for heart valve prostheses, the holder including:

a hub portion having a longitudinal axis, an engagement portion coupled to the hub portion (2) and including a plurality of finger members variably positionable relative to the hub portion between a collapsed condition wherein the finger members are closed onto the hub portion and an expanded condition wherein the finger members radially protrude with respect to the hub portion for engaging a heart valve prosthesis, wherein the finger members are L-shaped.

Embodiment 2 the holder of Embodiment 1, wherein the finger members are resiliently positionable relative to the hub portion.

Embodiment 3 the holder of any of Embodiments 1 or 2, wherein the L-shaped finger members include a body portion and a distal portion located at a distal end of the body portion and defining an axial abutment surface for a heart valve prosthesis.

Embodiment 4 the holder of Embodiment 3, wherein the body portion of the L-shaped finger members:
is substantially rectilinear, or
has a curvature in a radial plane of the holder.

Embodiment 5 the holder of Embodiment 4, wherein the body portion of the L-shaped finger members has a curvature in a radial plane of the holder, whereby the body portion of the L-shaped finger members has a concave outer surface and a convex inner surface.

Embodiment 6 the holder of any of the previous Embodiments, including three finger members equally angularly spaced around the hub portion.

Embodiment 7 the holder of any of the previous Embodiments, wherein the hub portion includes a cylindrical body, wherein the finger members are connected to the hub portion at the cylindrical body, the cylindrical body further including a plurality of radially protruding formations.

Embodiment 8 the holder of Embodiment 7, wherein the radially protruding formations are arranged at different axial positions along a longitudinal axis of the holder.

Embodiment 9 the holder of Embodiment 8, wherein the cylindrical body of the hub portion includes first radially protruding formations and second radially protruding formations at opposite axial ends thereof, wherein the first radially protruding formations are arranged at the axial end of the cylindrical body of the hub portion at which the finger members are connected.

Embodiment 10 the holder of any of the previous embodiments, wherein the finger members are configured for snap-fit engagement with the hub portion so as to maintain the finger members in the collapsed condition.

Embodiment 11 a heart valve prosthesis storage arrangement including:
a container with a filling of a storage solution for heart valve prostheses,
an expandable heart valve prosthesis having an armature, the expandable heart valve prosthesis being held within the container with a filling of a storage solution by means of a holder according to any of Embodiments 1 to 10, wherein the holder is in the expanded condition and the heart valve prosthesis is supported within the container by the armature of the heart valve prosthesis resting on the distal ends of the finger members of the holder.

Embodiment 12 a storage arrangement according to Embodiment 11, further including a support member coupled to the holder, the support member furthermore including retention means to restrain lifting of the heart valve prosthesis away from the distal ends of the finger members of the holder.

Embodiment 13 a storage arrangement according to Embodiment 11 or Embodiment 12, wherein the retention means include suture threads.

Embodiment 14 a storage arrangement according to any of Embodiments 11 to 13, wherein the heart valve prosthesis is an expandable aortic valve prosthesis including an armature with an inflow ring and an outflow ring connected by means of struts for holding a biological valve and by means of outwardly bulging anchoring formations, wherein the heart valve prosthesis is supported within the container by the outflow ring of the heart valve prosthesis resting on the distal ends of the finger members of the holder.

Embodiment 15 a delivery instrument for expandable heart valve prostheses, wherein:
the delivery instrument includes a handle, a shaft, and a delivery sheath displaceable along a longitudinal axis of the delivery instrument,
the shaft includes a connector member and a funnel shaped member coupled to the delivery sheath, the connector member coupleable to a holder according to any of Embodiments 1 to 10 with a heart valve prosthesis coupled thereto, with the delivery sheath in a fully retracted position,
the delivery sheath is displaceable axially towards a fully advanced position, whereby the relative movement between the funnel shaped member and the heart valve prosthesis coupled to the holder results in a radial contraction of the heart valve prosthesis and loading of the same into the delivery sheath.

Embodiment 16 a kit for crimping, loading and delivering expandable heart valve prostheses, the kit including:
a storage arrangement according to any of Embodiments 11 to 14,
a loading fixture configured to mate with the holder with the heart valve prosthesis coupled thereto, and
a delivery instrument, wherein the delivery instrument includes a handle, a shaft, and a delivery sheath displaceable along a longitudinal axis of the delivery instrument, wherein the shaft includes a connector member configured for mating with the holder and a funnel shaped member coupled to the delivery sheath, and further wherein:

the delivery instrument is configured to mate with the holder, already mating with the loading fixture, with the delivery sheath in a fully retracted position, when the delivery sheath is displaced axially towards a fully advanced position, the relative movement between the funnel shaped member and the heart valve prosthesis coupled to the holder results in a radial contraction of the heart valve prosthesis and loading of the same into the delivery sheath.

Embodiment 17 a method of crimping a heart valve prosthesis including:
providing a kit according to Embodiment 16,
extracting the holder having the heart valve prosthesis coupled thereto from the container of the storage arrangement,
mating the holder having the heart valve prosthesis coupled thereto with the loading fixture,
mating the connector member of the shaft of the delivery instrument with the holder, wherein the delivery sheath is in a fully retracted position,
displacing the delivery sheath axially towards a fully advanced position so that the relative movement between the funnel shaped member and the heart valve prosthesis coupled to the holder results in a radial contraction of the heart valve prosthesis and loading of the same into the delivery sheath.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A kit for delivering expandable heart valve prostheses, the kit comprising:
a heart valve prosthesis storage system comprising:
a container with a filling of a storage solution for heart valve prostheses;
an expandable heart valve prosthesis having an armature, the expandable heart valve prosthesis being held within the container with the filling of the storage solution by means of a holder comprising:
a hub portion having a longitudinal axis; and
an engagement portion coupled to the hub portion and including a plurality of finger members variably positionable relative to the hub portion between a collapsed condition, wherein the finger members are closed onto the hub portion, and an expanded condition, wherein the finger members radially protrude with respect to the hub portion for engaging a heart valve prosthesis, wherein the finger members are L-shaped and include proximal ends coupled to the hub portion and distal ends opposite the proximal ends;

wherein the holder is in the expanded condition and the heart valve prosthesis is supported within the container by the armature of the heart valve prosthesis resting on the distal ends of the finger members of the holder; and
a delivery instrument that includes a handle, a shaft, and a delivery sheath displaceable along a longitudinal axis of the delivery instrument, wherein the shaft includes a connector member configured for mating with the holder and a funnel shaped member coupled to the delivery sheath.

2. The kit of claim 1, further comprising a support member coupled to the holder, the support member including a restraining means to restrain lifting of the heart valve prosthesis away from the distal ends of the finger members of the holder.

3. The kit of claim 2, wherein the restraining means includes suture threads.

4. The kit of claim 1, wherein the heart valve prosthesis is an expandable aortic valve prosthesis, the armature including an inflow ring and an outflow ring connected by means of struts for holding a biological valve and by means of outwardly bulging anchoring formations, wherein the heart valve prosthesis is supported within the container by the outflow ring of the heart valve prosthesis resting on the distal ends of the finger members of the holder.

5. A kit for delivering expandable heart valve prostheses, the kit comprising:
a delivery instrument for expandable heart valve prostheses, the delivery instrument comprising:
a handle;
a shaft; and
a delivery sheath displaceable along a longitudinal axis of the delivery instrument;
wherein the shaft includes a connector member and a funnel shaped member coupled to the delivery sheath, the connector member coupleable to a holder comprising:
a hub portion having a longitudinal axis; and
an engagement portion coupled to the hub portion and including a plurality of finger members variably positionable relative to the hub portion between a collapsed condition, wherein the finger members are closed onto the hub portion, and an expanded condition, wherein the finger members radially protrude with respect to the hub portion for engaging a heart valve prosthesis, wherein the finger members are L-shaped;
wherein a heart valve prosthesis is coupled to the holder, with the delivery sheath in a fully retracted position, and the delivery sheath is displaceable axially towards a fully advanced position, whereby the relative movement between the funnel shaped member and the heart valve prosthesis coupled to the holder results in a radial contraction of the heart valve prosthesis and loading of the heart valve prosthesis into the delivery sheath; and
a heart valve prosthesis storage system comprising a container with a filling of a storage solution, the heart valve prosthesis being held within the container with the filling of the storage solution by the holder.

6. The kit of claim 5, wherein the finger members are resiliently positionable relative to the hub portion.

7. The kit of claim 5, wherein the L-shaped finger members include a body portion and an end portion located at one end of the body portion and defining an axial abutment surface for a heart valve prosthesis.

8. The kit of claim 7, wherein the body portion of each of the L-shaped finger members is substantially rectilinear.

9. The kit of claim 7, wherein the body portion of each of the L-shaped finger members has a curvature in a radial plane of the holder.

10. The kit of claim 9, wherein the body portion of each of the L-shaped finger members has a concave outer surface and a convex inner surface.

11. The kit of claim 5, wherein the plurality of finger members includes three finger members equally angularly spaced around the hub portion.

12. A kit for crimping, loading and delivering expandable heart valve prostheses, the kit comprising:
a storage system comprising:
a container with a filling of a storage solution for heart valve prostheses;
an expandable heart valve prosthesis having an armature, the expandable heart valve prosthesis being held within the container with the filling of the storage solution by means of a holder comprising:
a hub portion having a longitudinal axis; and
an engagement portion coupled to the hub portion and including a plurality of finger members variably positionable relative to the hub portion between a collapsed condition, wherein the finger members are closed onto the hub portion, and an expanded condition, wherein the finger members radially protrude with respect to the hub portion for engaging a heart valve prosthesis, wherein the finger members are L-shaped and include proximal ends coupled to the hub portion and distal ends opposite the proximal ends;
wherein the holder is in the expanded condition and the heart valve prosthesis is supported within the container by the armature of the heart valve prosthesis resting on the distal ends of the finger members of the holder;
a loading fixture configured to mate with the holder with the heart valve prosthesis coupled thereto; and
a delivery instrument;
wherein the delivery instrument includes a handle, a shaft, and a delivery sheath displaceable along a longitudinal axis of the delivery instrument;
wherein the shaft includes a connector member configured for mating with the holder and a funnel shaped member coupled to the delivery sheath; and
further wherein the delivery instrument is configured to mate with the holder, already mating with the loading fixture, with the delivery sheath in a fully retracted position, when the delivery sheath is displaced axially towards a fully advanced position, the relative movement between the funnel shaped member and the heart valve prosthesis coupled to the holder results in a radial contraction of the heart valve prosthesis and loading of the heart valve prosthesis into the delivery sheath.

13. The kit of claim 12, wherein the hub portion includes a cylindrical body, wherein the finger members are connected to the hub portion at the cylindrical body, the cylindrical body further including a plurality of radially protruding formations.

14. The kit of claim 13, wherein the radially protruding formations are arranged at different axial positions along a longitudinal axis of the holder.

15. The kit of claim 14, wherein the cylindrical body of the hub portion includes first radially protruding formations and second radially protruding formations at opposite axial ends thereof, wherein the first radially protruding formations are arranged at the axial end of the cylindrical body of the hub portion at which the finger members are connected.

16. The kit of claim 12, wherein the finger members are configured for snap-fit engagement with the hub portion so as to maintain the finger members in the collapsed condition.

17. The kit of claim 12, further comprising a support member coupled to the holder, the support member including a restraining means to restrain lifting of the heart valve prosthesis away from the distal ends of the finger members of the holder.

18. The kit of claim 17, wherein the restraining means includes suture threads.

19. The kit of claim 12, wherein the heart valve prosthesis is an expandable aortic valve prosthesis, the armature including an inflow ring and an outflow ring connected by means of struts for holding a biological valve and by means of outwardly bulging anchoring formations, wherein the heart valve prosthesis is supported within the container by the outflow ring of the heart valve prosthesis resting on the distal ends of the finger members of the holder.

20. A method of crimping a heart valve prosthesis, the method comprising the steps of:
providing a kit comprising:
a storage system comprising:
a container with a filling of a storage solution for heart valve prostheses;
an expandable heart valve prosthesis having an armature, the expandable heart valve prosthesis being held within the container with the filling of the storage solution by means of a holder comprising:
a hub portion having a longitudinal axis; and
an engagement portion coupled to the hub portion and including a plurality of finger members variably positionable relative to the hub portion between a collapsed condition, wherein the finger members are closed onto the hub portion, and an expanded condition, wherein the finger members radially protrude with respect to the hub portion for engaging a heart valve prosthesis, wherein the finger members are L-shaped and include proximal ends coupled to the hub portion and distal ends opposite the proximal ends;
wherein the holder is in the expanded condition and the heart valve prosthesis is supported within the container by the armature of the heart valve prosthesis resting on the distal ends of the finger members of the holder;
a loading fixture configured to mate with the holder with the heart valve prosthesis coupled thereto; and
a delivery instrument;
wherein the delivery instrument includes a handle, a shaft, and a delivery sheath displaceable along a longitudinal axis of the delivery instrument;
wherein the shaft includes a connector member configured for mating with the holder and a funnel shaped member coupled to the delivery sheath; and
further wherein the delivery instrument is configured to mate with the holder, already mating with the loading fixture, with the delivery sheath in a fully retracted position, when the delivery sheath is displaced axially towards a fully advanced position, the relative movement between the funnel shaped member and the heart valve prosthesis coupled to the holder results in a radial contraction of the heart valve prosthesis and loading of the heart valve prosthesis into the delivery sheath;

extracting the holder having the heart valve prosthesis coupled thereto from the container of the storage system;

mating the holder having the heart valve prosthesis coupled thereto with the loading fixture;

mating the connector member of the shaft of the delivery instrument with the holder, wherein the delivery sheath is in a fully retracted position; and displacing the delivery sheath axially towards a fully advanced position so that the relative movement between the funnel shaped member and the heart valve prosthesis coupled to the holder results in a radial contraction of the heart valve prosthesis and loading of the heart valve prosthesis into the delivery sheath.

* * * * *